US012788927B1

(12) United States Patent
Luo

(10) Patent No.: US 12,788,927 B1
(45) Date of Patent: Nov. 10, 2026

(54) ORONASAL MASK STABILIZATION SYSTEM

(71) Applicant: DCSTAR INC, New York, NY (US)

(72) Inventor: David Luo, New York, NY (US)

(73) Assignee: DCSTAR INC., New York, NY (US)

( * ) Notice: Subject to any disclaimer, the term of this patent is extended or adjusted under 35 U.S.C. 154(b) by 0 days.

(21) Appl. No.: 19/345,730

(22) Filed: Sep. 30, 2025

(51) Int. Cl.
*A61M 16/06* (2006.01)

(52) U.S. Cl.
CPC .... *A61M 16/0683* (2013.01); *A61M 16/0616* (2014.02); *A61M 2210/0618* (2013.01); *A61M 2210/0625* (2013.01)

(58) Field of Classification Search
CPC .......... A61M 16/0683; A61M 16/0616; A61M 2210/0618; A61M 2210/0625
See application file for complete search history.

(56) References Cited

U.S. PATENT DOCUMENTS

2014/0144448 A1 * 5/2014 Eifler .................... A61M 16/06 128/206.24
2022/0111171 A1 * 4/2022 Eves ................ A61M 16/0622

* cited by examiner

*Primary Examiner* — Elliot S Ruddie
(74) *Attorney, Agent, or Firm* — HSML P.C.

(57) ABSTRACT

An oronasal mask stabilization system configured to form a seal around the facial region of a patient's airway entrance and stabilize on the patient's face to create a breathable gas channel. The system includes a support member comprising a main body portion and a mask stabilizer, and a sealing formation structure connected to the support member for sealing engagement with the patient's face. The sealing formation structure is characterized in that its top portion contacts the nasal bridge below the nasal root and above the nasal tip to form a seal, while its bottom portion seals the mandibular region. This design maintains the stability of the pressurized chamber while ensuring effective sealing at both the nasal bridge and mandibular regions, thereby improving comfort, reducing leakage, and accommodating diverse facial features.

23 Claims, 18 Drawing Sheets

ORONASAL MASK STABILIZATION SYSTEM

TECHNICAL FIELD

The present disclosure relates to the technical field of respiratory assistance devices, and more specifically, to an oronasal mask stabilization system. The oronasal mask stabilization system of the present disclosure enhances its functionality by changing the structure of the sealing formation structure and the mask stabilizer, thereby achieving a more comfortable wearing experience and a better use effect than existing oronasal mask stabilization systems on the market. Its sealing performance is also improved to a certain extent. Moreover, the oronasal mask stabilization system is also suitable for patients who are not fitted with the existing oronasal mask stabilization systems on the market, thus expanding the user base and providing advantages in multiple aspects.

BACKGROUND

Sleep is a vital part of daily life. People spend approximately one-third of their time sleeping, and sleep is crucial for many brain functions, helping to restore the immune, nervous, skeletal, and muscular systems. However, some people suffer from sleep disorders such as insomnia, sleep apnea, or narcolepsy, leading to poor sleep quality or chronic sleep deprivation. These conditions can cause problems like poor concentration, slowed reactions, and a weakened immune system, and they also increase the risk of cardiovascular diseases, hypertension, and diabetes. To ensure proper sleep, patients require lifelong care or treatment. For sleep apnea patients, a common treatment is Positive Airway Pressure (PAP) therapy, most often Continuous Positive Airway Pressure (CPAP). This method delivers positive pressure breathing gas from a flow generator to the patient's airway to treat the sleep breathing disorder.

CPAP is a non-invasive respiratory support technique that prevents upper airway collapse and maintains an open airway by continuously delivering a constant level of positive airflow to the patient's airway throughout their spontaneous breathing cycle. It uses a ventilator to continuously deliver a constant positive pressure airflow to the patient's airway through a mask or nasal mask. Its core principle is to maintain a pressure higher than atmospheric pressure throughout the entire breathing cycle (including inhalation and exhalation) to prevent the collapse of the upper airway. It is primarily used to treat Obstructive Sleep Apnea Syndrome (OSA), a condition caused by the relaxation of upper airway muscles during sleep, leading to repeated apneas and hypoventilation. Additionally, CPAP is also suitable for other conditions that cause alveolar collapse or respiratory failure, such as Acute Respiratory Distress Syndrome (ARDS) and cardiogenic pulmonary edema. By improving the ventilation/blood flow ratio, reducing intrapulmonary shunting, and decreasing the work of breathing, it significantly enhances blood oxygen saturation and alleviates hypoxemia.

Mask accessories play a crucial role in CPAP therapy. They not only directly relate to the stability of the treatment effect and patient compliance but also profoundly affect the patient's comfort and quality of daily life. A well-designed, highly-fitting, and easy-to-adjust and clean mask accessory can effectively reduce air leaks, pressure marks, and skin discomfort, improving the night-time wearing experience and thereby increasing treatment compliance and long-term efficacy. However, existing mask accessories still have room for improvement in terms of adaptability, quietness, lightweight design, and convenience. There is an urgent need for design innovation through structural optimization, material upgrades, and user feedback-driven approaches to enhance their adaptability and ease of use for a diverse population, making CPAP therapy more personalized, comfortable, and integrated into daily life.

Therefore, there is an urgent need for technological iteration of existing CPAP mask systems to develop an improved oronasal mask stabilization system with higher conformity, structural stability, and user-friendliness to meet the needs of different ethnic and individual users, improve the treatment experience, and expand its clinical application value.

SUMMARY

The present disclosure is based on the aforementioned background needs, providing an oronasal mask stabilization system with better sealing performance and a more comfortable wearing experience. Its structural design represents a significant improvement over the oronasal mask stabilization systems and nasal masks currently on the market, effectively enhancing the device's adaptability, sealing, stability, and functional expandability in practical use. It possesses significant technical progress and value for widespread application.

Based on the aforementioned shortcomings, the present disclosure provides an oronasal mask stabilization system with adaptability, sealing, stability, and functional expandability.

The disclosure discussed herein provides an oronasal mask stabilization system, configured to form a seal around a facial region of an airway inlet of a patient and to stabilize a breathable gas passage against the patient's face. The oronasal mask stabilization system includes:

- a support member, configured to have a curvature at least partially facing the patient; and
- a sealing formation structure, configured to connect with the support member and seal against the patient's face.

The sealing formation structure having a top portion and a bottom portion, the top portion configured to contact a nasal bridge of the patient during use and to form a seal below a nasal root and above a nasal tip, and the bottom portion configured to contact and seal against a mandibular region of the patient.

The sealing formation structure having a first side in contact with the patient's face and a second side connected to the support member, the first side including at least one opening, the at least one opening including a nasal receiving region and an oral receiving region.

The nasal receiving region at least comprising a nasal tip and nasal alae, the nasal receiving region having flaps provided on the left and right sides, the flaps configured to conform to the nasal alae of the patient during use.

In an embodiment, the support member includes a main body portion and a mask stabilizer, the mask stabilizer configured to be connected to the main body portion in a front-to-back manner.

In an embodiment, in a front orthogonal view, a maximum distance between an outer contour of the mask stabilizer and an outer contour of the sealing formation structure is less than or equal to 3 mm.

In an embodiment, the support member is at least partially a rigid member.

In an embodiment, the sealing formation structure includes at least three regions having different thicknesses.

The disclosure discussed herein provides another oronasal mask stabilization system, configured to form a seal around a facial region of an airway inlet of a patient and to stabilize a breathable gas passage against the patient's face. The oronasal mask stabilization system includes:

- a support member, configured to have a curvature at least partially facing the patient; and
- a sealing formation structure, configured to connect with the support member and seal against the patient's face.

The sealing formation structure having a top portion and a bottom portion, the top portion configured to contact a nasal bridge of the patient during use and to form a seal below a nasal root and above a nasal tip, and the bottom portion configured to contact and seal against a mandibular region of the patient.

The sealing formation structure having a first side in contact with the patient's face and a second side connected to the support member, the first side including at least one opening, the at least one opening including a nasal receiving region and an oral receiving region.

The nasal receiving region having a curvature at least in a portion provided at the edge of the opening, the curvature extending toward the pressurized space.

The sealing formation structure including at least three regions having different thicknesses, including thin regions at the top portion and the bottom portion, a thick region at an intermediate region between the first side and the second side, and a thickest region provided between the thick region and the second side.

In an embodiment, the support member includes a main body portion and a mask stabilizer, the mask stabilizer configured to be connected to the main body portion in a front-to-back manner.

In an embodiment, in a front orthogonal view, a maximum distance between an outer contour of the mask stabilizer and an outer contour of the sealing formation structure is less than or equal to 3 mm.

In an embodiment, the thin region has a uniform wall thickness.

In an embodiment, the thick region has a uniform wall thickness.

In an embodiment, the sealing formation structure has a gradient wall thickness at least in part.

In an embodiment, the sealing formation structure includes four regions having different thicknesses.

The disclosure discussed herein provides yet another oronasal mask stabilization system, configured to form a seal around a facial region of an airway inlet of a patient and to stabilize a breathable gas passage against the patient's face. The oronasal mask stabilization system includes:

- a support member, configured to have a curvature at least partially facing the patient. The support member includes a main body portion and a mask stabilizer. The mask stabilizer is connected to the main body portion in a front-to-back manner; and
- a sealing formation structure, configured to connect with the support member and seal against the patient's face. The sealing formation structure has a top portion and a bottom portion. The top portion contacts a nasal bridge of the patient during use and forms a seal below a nasal root and above a nasal tip. The bottom portion contacts and seals against a mandibular region of the patient.

The sealing formation structure has a first side in contact with the patient's face and a second side connected to the support member. The first side includes at least one opening. The at least one opening includes a nasal receiving region and an oral receiving region.

The oronasal mask stabilization system has a width-to-length ratio of not greater than 1.5.

In an embodiment, at least a portion of the main body portion is at least partially a flexible member.

In an embodiment, at least a portion of the main body portion is at least partially a rigid member or a semi-rigid member.

In an embodiment, the mask stabilizer is detachably connected to the main body portion.

In an embodiment, the mask stabilizer is non-detachably connected to the main body portion.

In an embodiment, the mask stabilizer is connected to the main body portion by mutually engaging configurations.

The disclosure discussed herein further provides an oronasal mask stabilization system, configured to form a seal around a facial region of an airway inlet of a patient and to stabilize a breathable gas passage against the patient's face. The oronasal mask stabilization system includes:

- a support member, configured to have a curvature at least partially facing the patient; and
- a sealing formation structure, configured to connect with the support member and seal against the patient's face.

The sealing formation structure has a top portion and a bottom portion. The top portion contacts a nasal bridge of the patient during use and forms a seal below a nasal root and above a nasal tip. The bottom portion contacts and seals against a mandibular region of the patient.

The sealing formation structure has a first side in contact with the patient's face and a second side connected to the support member. The first side has only one opening. The opening includes a nasal receiving region and an oral receiving region. The length of the oronasal mask stabilization system ranges from 3 cm to 10.5 cm.

In an embodiment, the support member includes a main body portion and a mask stabilizer. The mask stabilizer is connected to the main body portion in a front-to-back manner.

In an embodiment, in a front orthogonal view, a maximum distance between an outer contour of the mask stabilizer and an outer contour of the sealing formation structure is less than or equal to 3 mm.

In an embodiment, the sealing formation structure includes at least three regions having different thicknesses.

In an embodiment, at least a portion of the sealing formation structure has an abrupt change in wall thickness.

The oronasal mask stabilization system of the present disclosure provides at least the following beneficial effects:

1. By optimizing the structure and streamlining the materials of the oronasal mask stabilization system, the present disclosure achieves an overall lightweight design without including sealing performance or support strength. This significantly reduces the pressure load on the facial soft tissues, bony prominences (such as the nasal bridge), and the face during use. The lightweight system not only reduces fatigue and discomfort from prolonged wear but also lowers the risk of pressure-related skin complications like pressure injuries, red marks, and pressure ulcers. This is particularly beneficial for patients with respiratory diseases who need long-term continuous positive pressure ventilation therapy. Furthermore, compared to traditional systems where the sealing point is at the nasal root, the present disclosure places the sealing point at the middle of the nasal bridge. This avoids obstructing the lower part of the eyes, expanding the wearer's horizontal and vertical field of view and increasing convenience. This provides the user with a better visual experience during daily activities like reading, walking, and communicating, enhancing the overall convenience and comfort. Consequently, this optimized design makes the mask more suitable for continuous wear across various times and scenarios in both clinical and home applications, offering higher ergonomic adaptability and patient compliance.

2. In the development process, controlling the curvature of the top region presented a significant and highly challenging technical difficulty. The present disclosure addresses the widespread technical issue in the prior art where prolonged wear results in noticeable facial indentations and discomfort. Here, the top portion of the sealing formation structure has been highly optimized. This improvement is not a simple geometric adjustment but a systematic innovation based on multiple technical requirements for sealing stability, facial comfort, and material contact sensation in this region during long-term wear. The top portion's point of action is a critical area where the mask directly contacts and seals the face. The skin in this area is thin and sensitive, and the seal largely relies on the mask itself. In actual development, determining the top curvature required considering not only the geometric match with the facial contour but also the airflow sealing path, the material's deformation properties under varying environmental temperatures and humidity, and its rebound stability after prolonged stress. By extending the top sealing surface within a reasonable range and precisely adjusting its inclination angle, combined with multiple rounds of iteration and minor parameter debugging, including large-sample data collection and analysis across different regions, genders, and age groups, the disclosure successfully broke through the technical bottleneck common in existing market masks, which is "prone to facial indentations and decreased comfort during prolonged wear." Each subtle curvature adjustment required multiple rounds of wear testing, sealing performance evaluation, and skin pressure distribution tests. The entire optimization process consumed a significant amount of time and experimental resources. After hundreds or even thousands of comparisons and verifications of minor differences, an optimal balance was finally achieved in the top's extension length, inclination angle, and local curvature. This has created a significant performance difference from existing market masks in terms of long-term user compliance and experience, thereby achieving a qualitative improvement in technical effect.

3. Sealing performance is one of the core features of an oronasal mask stabilization system for ensuring treatment effectiveness and user safety during daily use. It is directly related to the efficiency of positive pressure airflow delivery, treatment stability, and user compliance. The present disclosure optimizes the sealing point by placing it in the central nasal bridge area. Compared to traditional designs where the sealing point is located at the nasal root, the former avoids the high-stress areas below the eye sockets and where the nasal bones protrude, where the skin covering is extremely thin and the contours change sharply. This design provides a more continuous and stable conforming contact surface, effectively reducing the risk of local lifting or air leakage caused by highly uneven facial structures. Furthermore, compared to structures with the sealing point at the nasal tip, the nasal tip is a dynamic area with highly elastic and variable soft tissues, making it difficult to achieve a stable seal. This often leads to frequent air leaks, pressure pain, or skin damage. In contrast, the central nasal bridge area has relatively thicker soft tissue and a stable shape that does not easily shift with facial expressions or sleeping positions. This area also has a higher structural tolerance and more lasting conformity. Therefore, the central nasal bridge sealing strategy adopted by the present disclosure demonstrates significant advantages in structural stability, human adaptability, and air-tightness maintenance, serving as a crucial guarantee for providing efficient, comfortable, and long-term ventilation support.

4. The present disclosure addresses the limitations of traditional oronasal mask stabilization systems in terms of structural stability and support performance through systematic structural optimization and functional improvements. By redesigning the layout of the sealing formation structure, adjusting the position and size ratio of the support frame, and introducing more ergonomic component forms, the overall system significantly enhances the stability and balanced support of the mask during use while maintaining sealing performance. Based on the improved oronasal mask stabilization system, the present disclosure introduces an optimized mask stabilizer that is adapted to it. This mask stabilizer is closer to the edge of the oronasal mask stabilization system compared to products on the market, which, on the basis of size adaptation, further increases its coverage area. The optimized structure can more effectively distribute the mask's weight and the reverse thrust generated by ventilation evenly across the mid-facial region. This avoids excessive load on local pressure points, reduces stress concentration on facial bony prominences, thereby alleviating discomfort and the risk of pressure injuries caused by long-term use. In addition, the improved support system has stronger geometric stability, maintaining a good fit even during changes in the user's body position, speech, or minor facial movements. It is less prone to displacement or air leakage, significantly enhancing the product's dynamic adaptability and clinical practicality. This structural design not only improves safety and comfort during use but also provides a more reliable support foundation for long-term wear in multiple scenarios.

5. The oronasal mask stabilization system provided by the present disclosure is more adaptable to a variety of face shapes, including but not limited to those with different nasal bridge heights, different nasal ala widths, and different facial prominences. It has a particular advantage for people with low nasal root or flat noses. The disclosure effectively avoids the issue of poor fit caused by variations in nasal root height and nasal ala size, thereby achieving good sealing conformity and air-tightness maintenance across different ethnic groups and populations. In addition, for individuals with congenital developmental abnormalities, the oronasal mask stabilization system avoids areas with significant variations, further enhancing its ethnic adaptability and conformity. Furthermore, the flaps structure described in the present disclosure have excellent adaptability. By introducing a flexible and adjustable flap material and structural layout, this component provides good sealing when conforming to the face. At the same time, while maintaining stable support, it can adapt to individual differences in facial width, high cheekbones, deep depressions, and other features, significantly improving wearing comfort and stability.

6. The oronasal mask stabilization system of the present disclosure significantly improves user operational efficiency. The oronasal mask stabilization system described herein can also be used in combination with a neck strap structure. As an optimization of the traditional head-strap fixation, this disclosure has multi-faceted advantages in structure, ergonomics, and user experience. Compared to traditional head-strap wear, the neck strap structure transfers the support points of the mask or related components from the head to the neck, which significantly reduces head pressure and wearing burden. This enhances wearing comfort and stability, making it particularly suitable for the elderly, individuals with sensitive heads, and those who need to wear it for long periods at night. Traditional head straps must wrap around the head, posing a risk of head compression or displacement regardless of sleeping position. Therefore, the system of the present disclosure facilitates changes in body position, such as sleeping on one's side or back. Furthermore, the introduction of the neck strap structure means the system does not need to be pulled over the head. Instead, it can be hung from the neck for initial positioning, making the operation more intuitive and especially suitable for the elderly or those with limited mobility. For users with long hair, the system will not mess up their hairstyle or leave marks. Overall, this structure provides a more ergonomic direction for the wearing method of mask-type devices.
7. The flap structure of the nasal sealing region, in conjunction with the redesigned sealing points, provides advantages in terms of airtightness, structural stability, wearing comfort, and adaptability of the oronasal mask stabilization system. As a locally extending, flexible conforming structure, the flaps can achieve more detailed wrapping and sealing compensation on both sides of the nasal alae, effectively enhancing airtightness and preventing air leakage caused by variations in face shape or dynamic facial expression changes. At the same time, the downward shift of the top of the sealing formation structure avoids areas of significant height difference at the nasal root and nasal dorsum, allowing the flaps to conform more closely to the natural curvature of the lateral nasal area. This further enhances the structural stability and wearing comfort of the mask. The flap structure provides a compensation mechanism that greatly improves the product's universality for use across different populations and scenarios.

DETAILED DESCRIPTION

Figure 1:
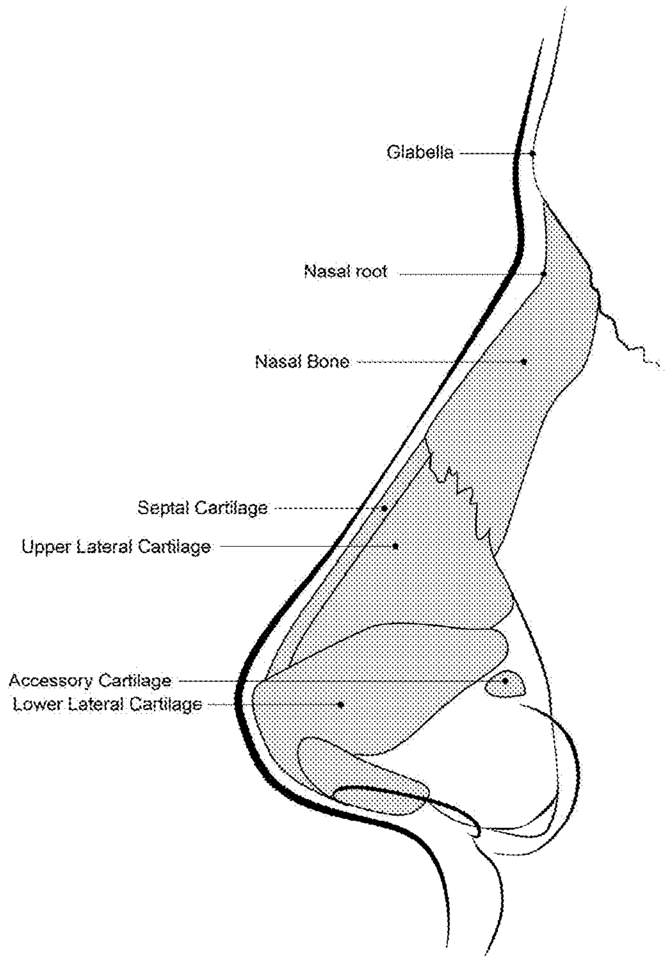
FIG. 1 is a simplified schematic view of a nasal structure.

To make the above-mentioned objectives, features, and advantages of the present disclosure more apparent and understandable, several specific embodiments are described in detail below with reference to the accompanying drawings. Numerous specific details are set forth in the following description in order to facilitate a full understanding of the present disclosure. However, the present disclosure may be practiced in many other manners different from those specifically described herein, and modifications of a similar nature may be made by those skilled in the art without departing from the spirit and scope of the present disclosure. Therefore, the present disclosure is not limited to the specific embodiments disclosed below.

Compared with conventional oronasal mask stabilization systems, the present disclosure provides improvements wherein the support member not only effectively maintains the geometric stability of the pressurized space but also provides stable support for the sealing formation structure. In addition, through optimized arrangement of the sealing positions, the mask can more accurately conform to the patient's facial contour during use, thereby balancing sealing performance with comfort, reducing concentrated pressure on the nasal bridge, periorbital region, and adjacent soft tissues, while lowering the risk of ocular interference and significantly broadening the range of patient applicability. With respect to the common problem of sealing pressure marks associated with long-term use, the present disclosure implements multiple rounds of optimization of the geometric contour of the curved surface of the top portion of the sealing formation structure, precisely defining critical curvature and dimensional parameters. As a result, a stable and comfortable sealing effect can be achieved across diverse facial features. Through the combination of the above-mentioned improvements, the present disclosure achieves comprehensive enhancement over conventional products in terms of wearing compliance, sealing reliability, structural stability, and user comfort, thereby attaining multiple performance balances that could not be simultaneously achieved in the prior art.

As shown in FIGS. 1 through 36, multiple perspective views, orthographic views, sectional views, and structural schematic diagrams of the oronasal mask stabilization system of the present disclosure are illustrated.

Several structural examples of the oronasal mask stabilization system of the present disclosure are described in detail below with reference to specific embodiments.

Embodiment 1

In this embodiment, an oronasal mask stabilization system 1 is provided. The oronasal mask stabilization system 1 includes: a support member 2 configured to have a curvature at least partially facing the patient; and a sealing formation structure 3 configured to be connected to the support member 2 and to seal against the patient's face. The sealing formation structure 3 is constructed to have a top portion 34 and a bottom portion 35. The top portion 34 is configured to contact the nasal bridge of the patient during use and to form a seal below the nasal root and above the nasal tip. The bottom portion 35 is configured to contact and seal against the mandibular region of the patient. The sealing formation structure 3 has a first side 31 configured to contact the patient's face, and a second side 32 configured to be connected to the support member 2. The first side 31 comprises at least one opening 33, the at least one opening 33 including a nasal receiving region 331 and an oral receiving region 332. The nasal receiving region 331 at least accommodates the nasal tip and alar portions of the patient's nose. Furthermore, the nasal receiving region 331 includes flaps 36 distributed on the left and right sides thereof, the flaps 36 being configured to fit against the nasal alae of the patient during use.

Specifically, in this embodiment, the oronasal mask stabilization system 1 of the present disclosure includes the support member 2 and the sealing formation structure 3. The support member 2 is configured to have a curvature at least partially facing the patient. In this embodiment, the support member 2 is at least partially formed as a rigid member. The advantage thereof is that it can provide stable morphological support and structural strength for the oronasal mask stabilization system 1, ensuring that the pressurized space maintains a fixed shape during use, thereby maintaining sealing performance and overall structural stability.

Figure 13:
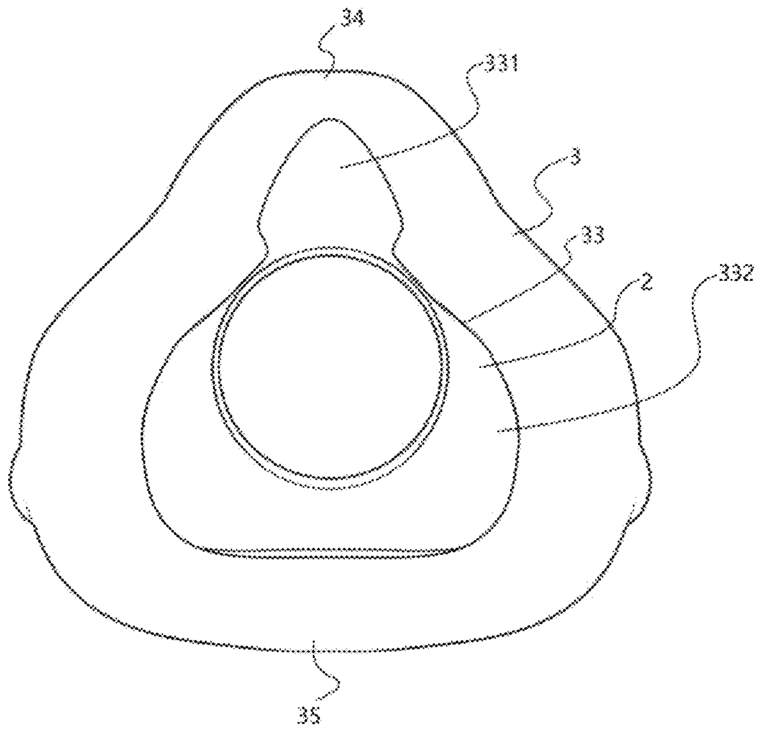
FIG. 13 is a schematic view illustrating a second form of an opening of a sealing formation structure in an embodiment of the present disclosure.

The sealing formation structure 3 is configured to be connected to the support member 2 and to seal against the patient's face. The sealing formation structure 3 has a first side 31 configured to contact the patient's face, and a second side 32 configured to be connected to the support member 2. The first side 31 includes at least one opening 33, the at least one opening 33 including a nasal receiving region 331 and an oral receiving region 332. In the present embodiment, the first side 31 is provided with one and only one continuous opening 33, which is configured to simultaneously surround both the nasal airway and the oral airway of the patient. The opening 33 may be triangular, oval, gourd-shaped, teardrop-shaped, or any other shape capable of encompassing both the nasal and oral airways. The opening 33 may be further divided into the nasal receiving region 331 and the oral receiving region 332 to achieve more precise fitting and sealing performance. Specifically, the nasal receiving region 331 may be configured as an integral smooth-curved opening 33. The nasal receiving region 331 at least includes the nasal tip and the nasal alae, and its contour may be arcuate, oval, or polygonal with slightly pointed corners (as shown in FIG. 13), in order to accommodate different nasal shapes and variations across ethnic groups. The oral receiving region 332 is connected to the nasal receiving region 331 and is located below the nasal receiving region 331. The oral receiving region 332 may be a laterally extended oval or rectangular shape, or it may adopt an opening 33 with flexible, contractible edges so as to cover and seal against the mandibular region of the patient, while ensuring unobstructed airflow during inhalation and exhalation. Furthermore, a transition region may be provided between the nasal receiving region 331 and the oral receiving region 332. The wall thickness and curvature of the transition region may gradually change, thereby providing improved wearing comfort while maintaining overall sealing performance. The transition region is formed by the edge of the opening 33 extending inward toward the center of the opening 33, in which the curved surfaces may contact one another without being physically joined. A continuous curved surface is formed between the first side 31 and the second side 32 of the sealing formation structure 3. During use, the continuous curved surface at least partially contacts and seals against the patient's face. The curvature of the surface is designed to accommodate different facial types and anatomical characteristics across populations, thereby ensuring effective airtightness and wearing comfort. The continuous curved surface may be formed as a single-layer structure or as a multilayer structure. The multilayer structure may include a combination of materials with different hardness or elasticity, so as to balance flexible conformity with overall structural support. To enhance durability and reliability, reinforcing ribs or rib-like structures may be provided on the inner side of the curved surface, in order to prevent the curved surface from excessive deformation, separation, or rupture under airflow pressure within the pressurized chamber.

Figure 2:
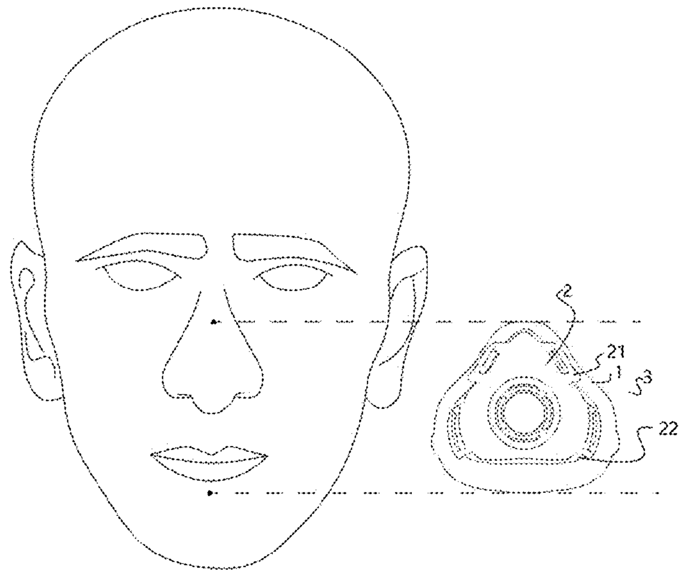
FIG. 2 is a schematic view illustrating a sealing area of an oronasal mask stabilization system according to multiple embodiments of the present disclosure.
Figure 8A:
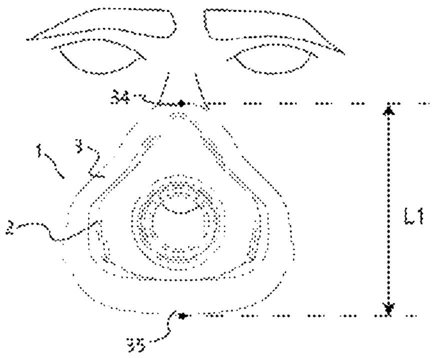
FIGS. 8A and 8B are schematic views comparing the sealing ranges of the oronasal mask stabilization system according to multiple embodiments of the present disclosure with that of a conventional oronasal mask stabilization system available on the market.
Figure 8B:
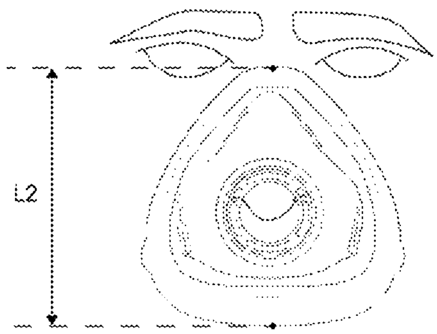
Figures 14A, 14B, 14C:
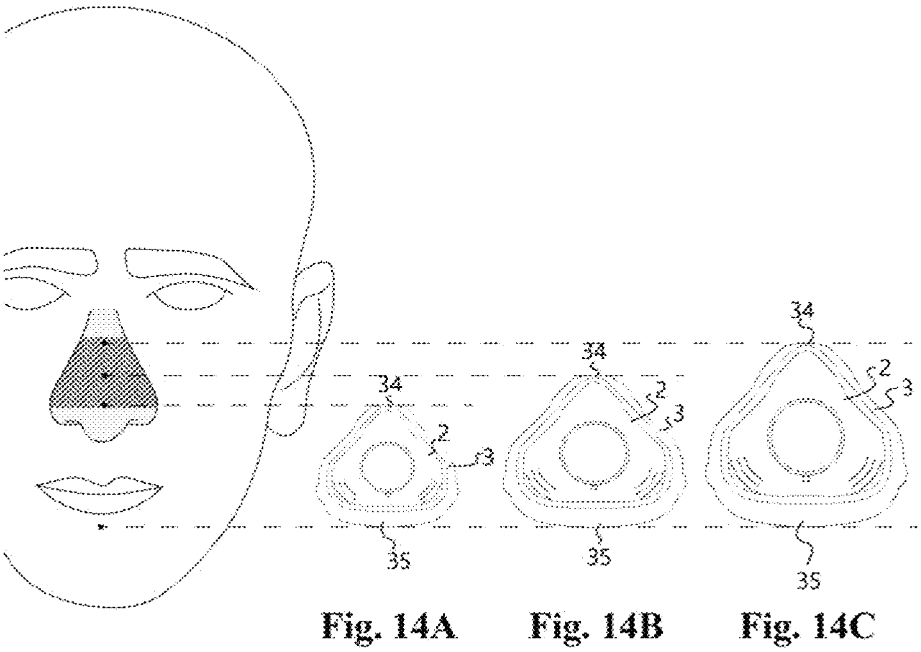
FIGS. 14A, 14B and 14C are schematic views further defining the sealing range of the oronasal mask stabilization system according to multiple embodiments of the present disclosure.
Figure 15:
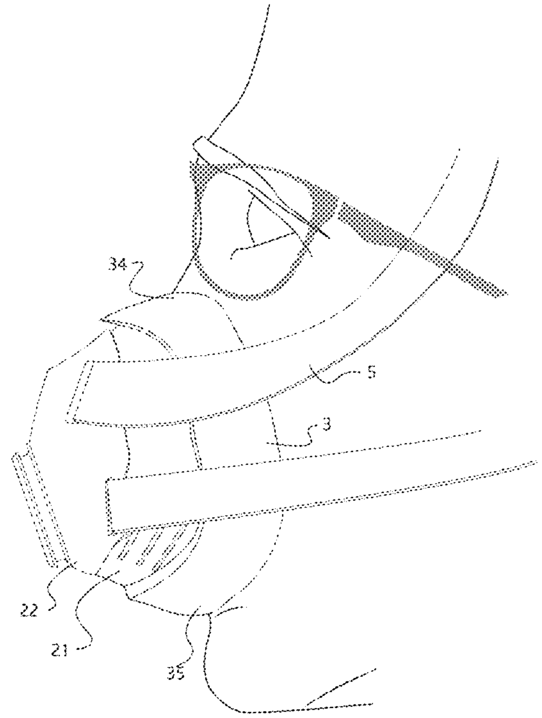
FIG. 15 is a schematic view illustrating that the oronasal mask stabilization system according to multiple embodiments of the present disclosure allows a space for accommodating ocular fitting components during use.

The sealing formation structure 3 is constructed to have a top portion 34 and a bottom portion 35. The top portion 34 is configured to contact the nasal bridge of the patient during use and to form a seal below the nasal root and above the nasal tip. The bottom portion 35 is configured to contact and seal against the mandibular region of the patient (i.e., the region of the vertebrate face, including humans, located below the lips). As shown in FIGS. 2, 8A and 8B, in FIGS. 8A and 8B, the sealing region length of the oronasal mask stabilization system 1 of the present disclosure is represented as L1, whereas the sealing region length of a conventional oronasal mask stabilization system 1 on the market is represented as L2, and L1<L2. This structure constitutes a key and innovative structural characteristics of the present disclosure, playing a central role in both the overall sealing performance of the mask and the wearing comfort. By relocating the sealing position of the top portion 34 to a region below the nasal root yet above the nasal tip, the disclosure effectively avoids the bony protrusion of the nasal root and the sensitive region of the infraorbital margin. This reduces localized compression on the nasal bridge and adjacent thin soft tissues, thereby lowering the risk of pressure marks and skin injury during prolonged wear. In addition, the design enhances adaptability across diverse facial profiles, including patients with low nasal roots, depressed noses, or congenital or postoperative nasal abnormalities, and provides space for wearing eyeglasses or other ocular assistive devices, thereby improving compatibility in daily use (as shown in FIGS. 14A, 14B and 14C). Further, the top portion 34 more specifically seals against the patient's nose at a position below 15% of the overall nasal bridge length measured from the radix and above 15% of the overall nasal bridge length measured from the nasal tip (as shown FIG. 15, the apex of the sealing formation structure 3 may form a seal with the patient's face at any position within this region). In conventional oronasal mask stabilization systems 1 available on the market, the sealing point of the mask is typically set at the nasal root of the nasal bridge, with airtightness depending on the fit between this region and the top portion 34 of the opening 33 of the sealing formation structure 3. However, due to significant variations in nasal bridge height and morphology among patients, this design presents multiple limitations in practical use. For patients with shorter or collapsed nasal bridges, the sealing point often fails to adequately conform to the facial contour, resulting in gaps around the nasal bridge that lead to localized air leakage, thereby reducing overall airtightness, affecting the stability of positive pressure delivered by the ventilator, and potentially diminishing therapeutic effectiveness. Conversely, for patients with higher or more prominent nasal bridges, the fixed sealing point at the radix may generate excessive localized pressure, causing concentrated skin loading that increases the risk of pressure marks, redness, or discomfort. Such excessive pressure may also cause displacement during use, adversely affecting sealing stability and treatment compliance.

Figure 16:
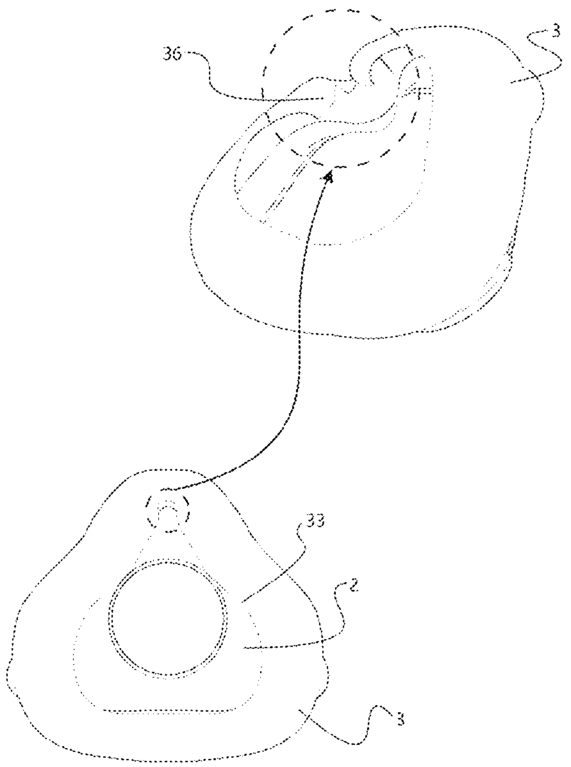
FIG. 16 is a schematic view of the oronasal mask stabilization system according to multiple embodiments of the present disclosure, illustrating a curvature extending from a top portion of the sealing formation structure toward a pressurized chamber.
Figure 17:
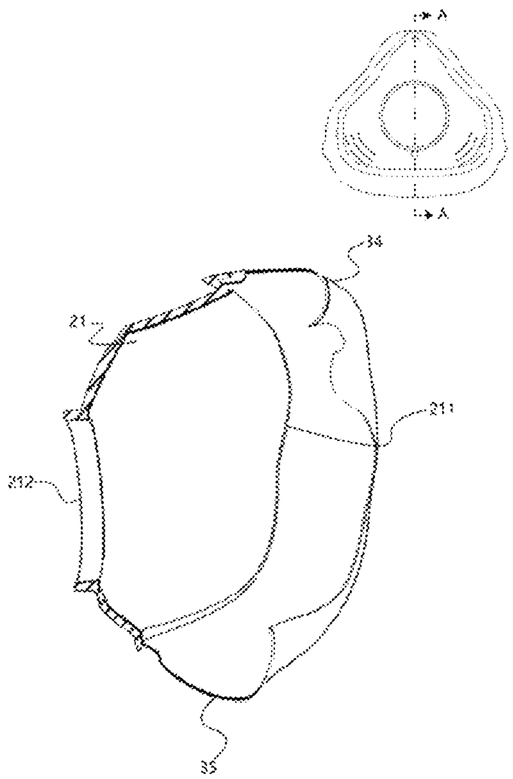
FIG. 17 is a cross-sectional view taken along a line A-A of the oronasal mask stabilization system according to multiple embodiments of the present disclosure.
Figure 18:
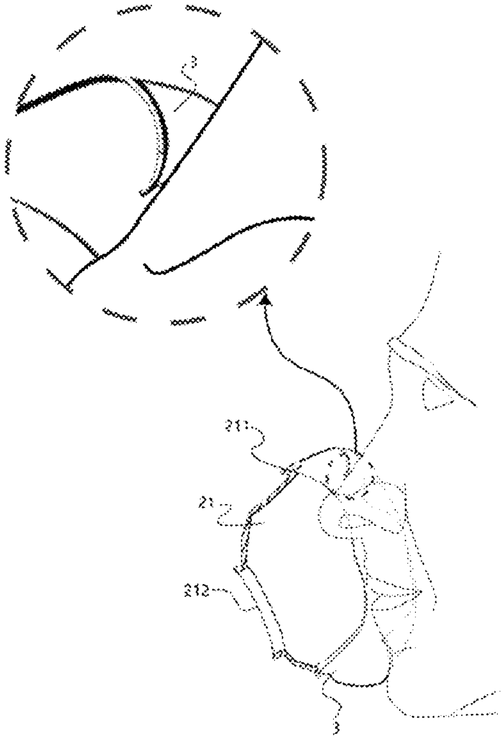
FIG. 18 is a schematic view illustrating improved wearing comfort of the oronasal mask stabilization system on a patient's face according to multiple embodiments of the present disclosure.
Figure 19:
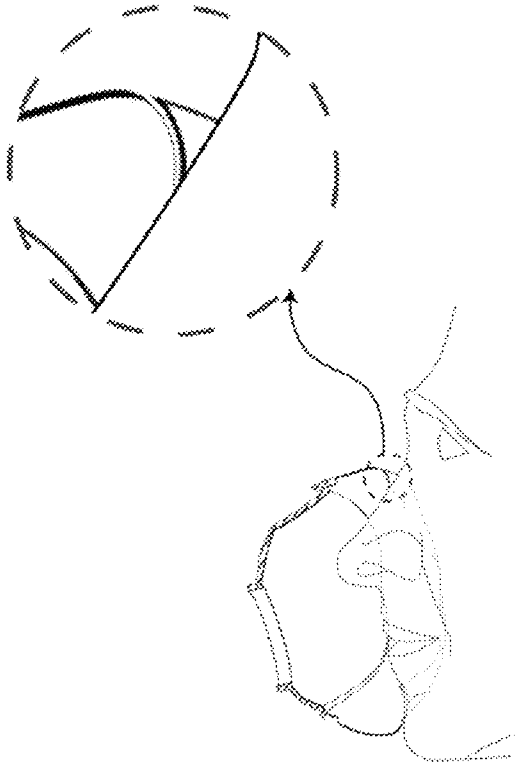
FIG. 19 is a schematic view of a conventional oronasal mask stabilization system available on the market showing a formation of pressure marks during use.

More importantly, through hundreds and even thousands of comparative tests and verifications of subtle variations, the present disclosure successfully overcomes a technical bottleneck commonly existing in similar oronasal mask stabilization systems 1 on the market, namely, the problem that prolonged wearing tends to cause noticeable pressure marks, skin erythema, and localized discomfort on the face, particularly in the nasal bridge region. In one specific implementation, the present disclosure introduces a targeted optimization of the top portion 34 of the sealing formation structure 3. While maintaining the overall geometric stability, the sealing surface length of the top portion 34 is appropriately extended toward the pressurized chamber within a reasonable range (as shown in FIGS. 16-18), with the extension length being at least 3 mm. By adjusting the angle and repeatedly calibrating and optimizing its curvature, the sealing surface is enabled to contact the patient's face in a surface-to-surface manner to distribute pressure, rather than in a line-to-face manner that concentrates pressure. This achieves a significant improvement in wearing comfort while maintaining good sealing performance. This improvement distinguishes the present disclosure from conventional oronasal mask stabilization systems on the market. Because the nasal bridge region extends into the pressurized chamber, conventional systems typically cause the edge of the opening at the top portion of the sealing formation structure to contact the nasal bridge at a nearly perpendicular angle during use. Under structural loading, such an angle readily generates concentrated pressure on the nasal bridge, which is the primary cause of pressure marks and discomfort (as shown in FIG. 19). The complexity of this issue is further heightened by the fact that the skin at the nasal bridge region is thinner, the underlying tissue is more fragile, and the area is densely innervated, making it more sensitive to external pressure compared with other facial regions. However, any adjustment of the angle of the top portion 34 of the sealing formation structure 3 in this region tends to result in deterioration or even failure of sealing performance. Consequently, this problem has long remained unresolved under conventional technical conditions. Existing manufacturing technologies and design concepts show significant limitations in research depth of angle control, process precision, and the balancing of comfort and sealing performance, such that no mature and stable solution has been available in the prior art. By contrast, the present disclosure introduces a breakthrough comprehensive design strategy combining precise angle control with extension of the sealing surface. Together with long-term iterative testing and rigorous error optimization, this approach ultimately achieves a significant reduction in localized pressure and pressure marks in the nasal bridge region, without sacrificing sealing performance (as shown in FIG. 18). This technical solution not only resolves a core difficulty that has troubled the industry for many years, but also provides a differentiated effect in user experience compared with conventional oronasal masks on the market.

Figure 20:
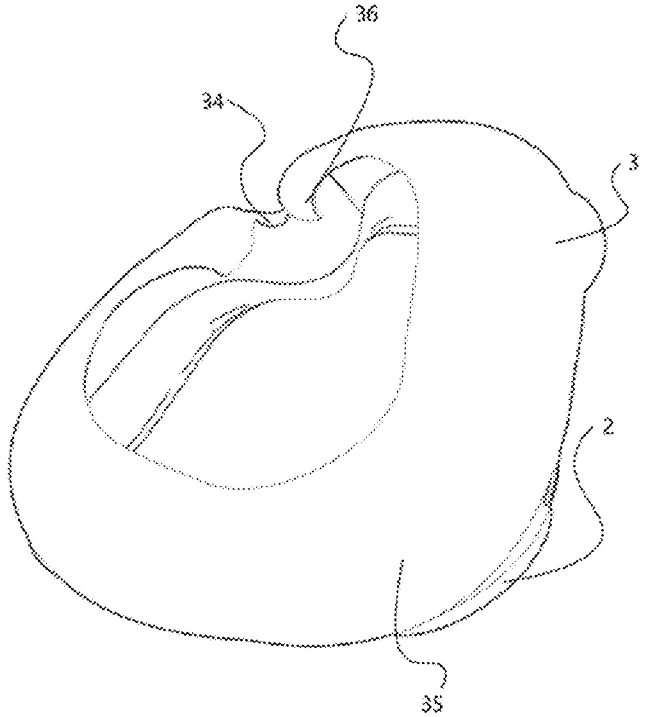
FIG. 20 is a schematic view of the sealing formation structure in an embodiment of the present disclosure showing flaps extending from a left side and a right side of an opening.

In the present embodiment, another inventive aspect is that the nasal receiving region 331 is provided, at least at a portion located at the edge of the opening 33, with a curvature extending toward the pressurized space. Furthermore, the nasal receiving region 331 includes flaps 36 distributed on the left and right sides, the flaps 36 being configured to conform to the nasal alae of the patient during use (as shown in FIG. 20). Specifically, the nasal receiving region 331 of the sealing formation structure 3 is precisely designed at a location near the edge of the opening 33 to form a spatial curved surface extending into the pressurized space. In some implementations, the curved surface may be embodied as a wing-like extension protruding inward from the edge. The extended curved surface is not a simple geometric bend but rather an optimized contour obtained through numerical optimization, thereby enabling large-area, smooth, and continuous contact with the nasal alae and surrounding soft tissues during wearing. The curvature portion can adapt, in a dynamic wearing state, to micro-deformations of the nasal alae and facial soft tissues caused by breathing or facial expression changes. By virtue of its flexible deformation and rebound characteristics, the curvature portion maintains a stable airtight interface between the sealing surface and the patient's skin. The curvature structure and the contour of the top portion 34 of the sealing formation structure 3 form a continuous spatial transition, cooperating in both morphology and function to construct a composite sealing surface covering the region from the nasal bridge to the nasal alae. This ensures stable sealing contact at a position below the nasal root and above the nasal tip, achieves three-dimensional enclosure of the nasal airway, and significantly improves both sealing performance and wearing comfort for the patient.

The sealing formation structure 3 is typically manufactured from a flexible material and possesses a certain degree of elasticity. The material may include rubber, silicone, elastomeric plastic, or the like. These materials exhibit excellent flexibility, resilience, and aging resistance, and are capable of withstanding long-term mechanical compression without significant deformation, while also providing skin compatibility and biocompatibility. Furthermore, in order to enhance fitting stability and anti-slip performance, the surface of the sealing formation structure 3 may be designed with micro-textures, grid-like patterns, or corrugated structures. Such surface configurations increase friction against the face during wearing and reduce the adverse effects of perspiration and skin oils on sealing performance. From a manufacturing perspective, the sealing formation structure 3 may be integrally molded from a single material to unify flexibility and airtightness, or it may be fabricated by multi-material co-molding or partial overmolding to achieve precise control of hardness, thickness, and surface texture in different regions. This enables the sealing formation structure 3 to meet diverse usage requirements and application scenarios.

Figure 24:
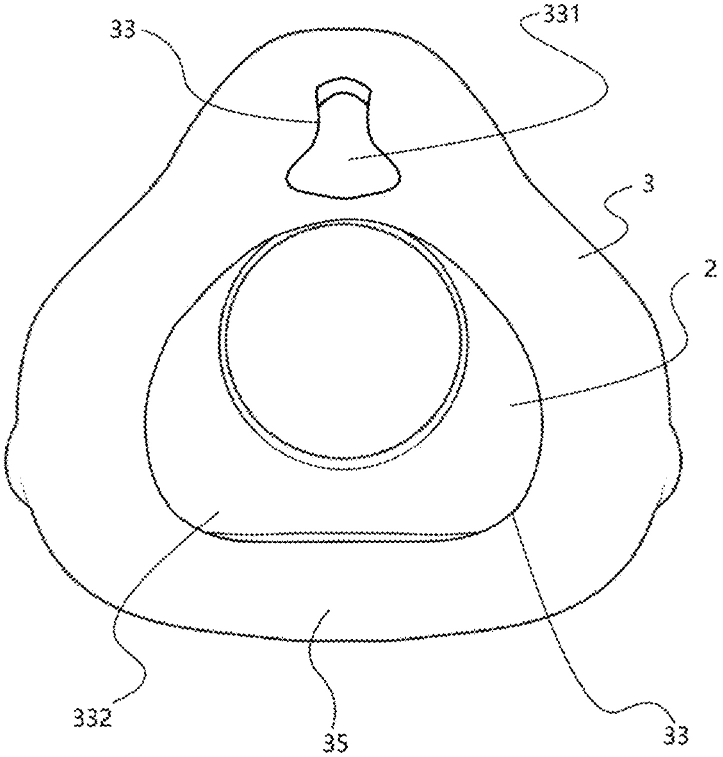
FIG. 24 is a schematic view of a nasal receiving region and an oral receiving region being independent and not interconnected to each other in an embodiment of the present disclosure.
Figure 25:
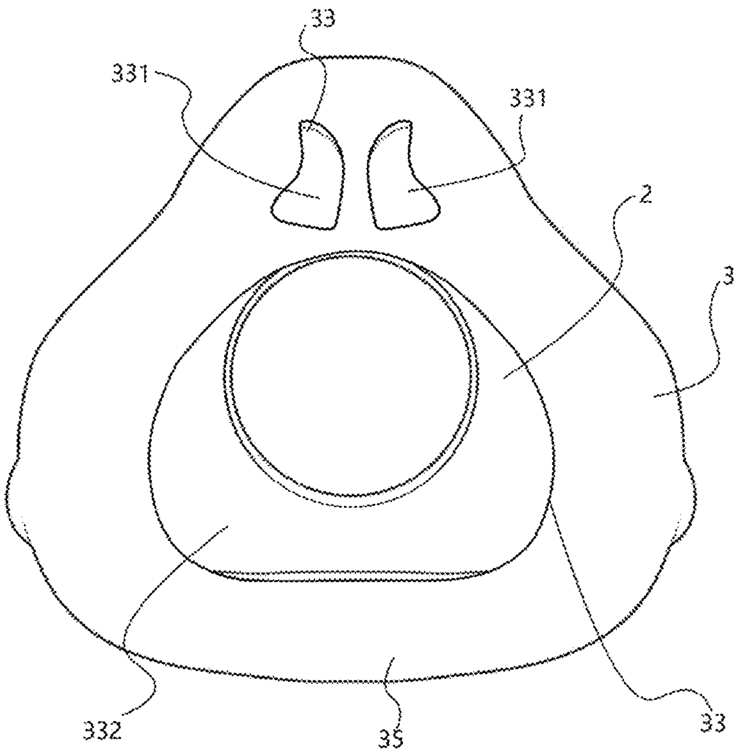
FIG. 25 is a schematic view of the opening being divided into two nasal receiving regions and one oral receiving region in an embodiment of the present disclosure.

In other implementations, the sealing formation structure 3 may have multiple configurations of the opening 33 on the first side 31. Such configurations may include a form in which the nasal receiving region 331 and the oral receiving region 332 are separate rather than continuous. That is, the sealing formation structure 3 includes two openings 33 on the first side 31, one corresponding to the nasal receiving region 331 and the other corresponding to the oral receiving region 332. In such a form, the first side 31 has at least two openings 33 (as shown in FIG. 24). Furthermore, the nasal receiving region 331 may be subdivided into a left nostril region and a right nostril region (as shown in FIG. 25). Such subdivision allows more precise matching with the patient's nasal airways, thereby preventing sealing failure caused by displacement during use. In other implementations, the nasal receiving region 331 and the oral receiving region 332 may be separated by a detachable or deformable partition member, such that the same oronasal mask stabilization system 1 can be converted, as needed, between a single-opening 33 mode and a multi-opening 33 mode, thereby accommodating different treatment protocols. The partition member may be formed of a flexible, semi-rigid, or rigid material, and may be secured to the sealing formation structure 3 by snap-fit, insertion, magnetic attraction, or thermal fusion, thereby facilitating replacement or adjustment. To further improve adaptability, the nasal opening 33 may be designed in the shape of an oval, circular, or irregular cross-section conforming to the contour of the nasal alae, while the oral opening 33 may adopt a regular rectangular, trapezoidal, or lip-conforming curved shape.

Figure 26:
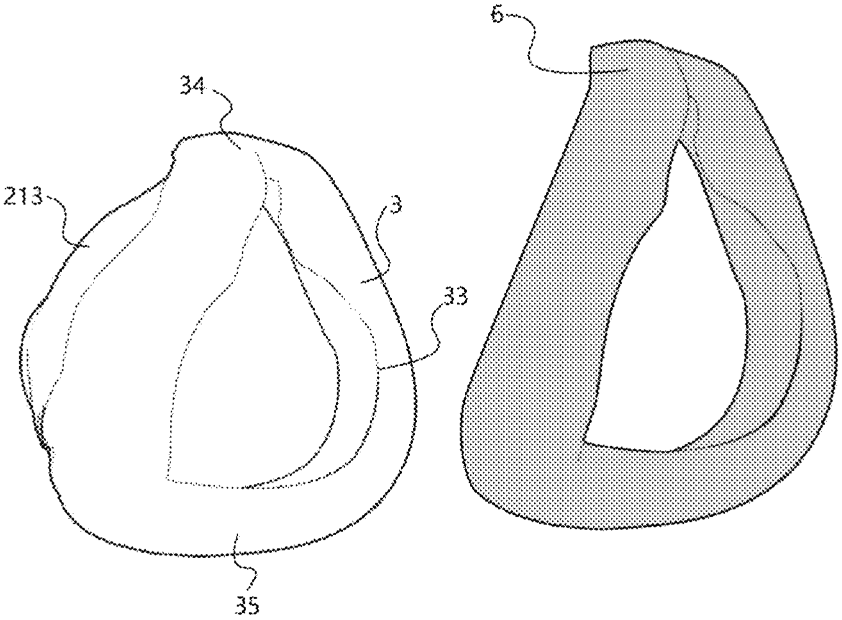
FIG. 26 is a schematic view of the oronasal mask stabilization system connected with a comfort layer in an embodiment of the present disclosure.

In some implementations, the sealing formation structure 3 is connected with a comfort layer 6, thereby forming a cushioned oronasal mask stabilization system 1 (as shown in FIG. 26). The comfort layer 6 may be fabric and/or foam. That is, the sealing formation structure 3 may be configured for use with fabric to improve patient wearing comfort, the sealing formation structure 3 may also be configured to connect with foam, and the sealing formation structure 3 may further be configured to connect with both fabric and foam. The sealing formation structure 3 provides attachment points for the comfort layer 6, which may be located on the surface or on the section, the two together forming a complete cushioning portion. The comfort layer 6 may be continuous or discontinuous, and may be of uniform thickness or non-uniform thickness. The material of the comfort layer 6 is required to be sterilization-resistant, breathable, absorbent, and biocompatible (exhibiting good biocompatibility without causing allergic reactions or other adverse effects, suitable for contact with the human body) and so on. The comfort layer 6 may be made from one or more natural fabrics or synthetic fibers such as cotton (soft and breathable), elastic silk fabric, wool, spandex, polyester elastic fiber, polyester fiber (wrinkle-resistant and abrasion-resistant), nylon fiber (high strength and abrasion-resistant), acrylic fiber (good elasticity and durability), or polypropylene fiber (lightweight and abrasion-resistant). The comfort layer 6 may also be manufactured with metallic fibers to provide different functional comfort layers 6, such as antibacterial fabric or antistatic fabric. Additionally, the comfort layer 6 may be foam material such as medical polyurethane sponge (lightweight, soft, biocompatible, and hypoallergenic), medical wax sponge (capable of absorbing liquid, suitable for wound dressings and hemostasis), polyether sponge (high elasticity and durability), or polyester sponge (lightweight and soft) and so on. The comfort layer 6 is fixed to the sealing formation structure 3 by adhesion using glue.

Embodiment 2

In this embodiment, an oronasal mask stabilization system 1 of the present disclosure is provided. The oronasal mask stabilization system 1 includes: a support member 2 configured to have a curvature at least partially facing the patient; wherein the support member 2 includes a main body portion 21 and a mask stabilizer 22, the mask stabilizer 22 being configured to be connected to the main body portion 21 in a front-to-back manner; and a sealing formation structure 3 configured to be connected to the support member 2 and to seal against the patient's face. The sealing formation structure 3 is constructed to have a top portion 34 and a bottom portion 35. The top portion 34 is configured to contact the nasal bridge of the patient during use and to form a seal below the nasal root and above the nasal tip. The bottom portion 35 is configured to contact and seal against the mandibular region of the patient. The sealing formation structure 3 has a first side 31 configured to contact the patient's face and a second side 32 configured to be connected to the support member 2. The first side 31 includes at least one opening 33, the at least one opening 33 including a nasal receiving region 331 and an oral receiving region 332. The nasal receiving region 331 at least includes the nasal tip and the nasal alae. Furthermore, the nasal receiving region 331 includes flaps 36 distributed on the left and right sides, the flaps 36 being configured to conform to the nasal alae of the patient during use.

Figure 3:
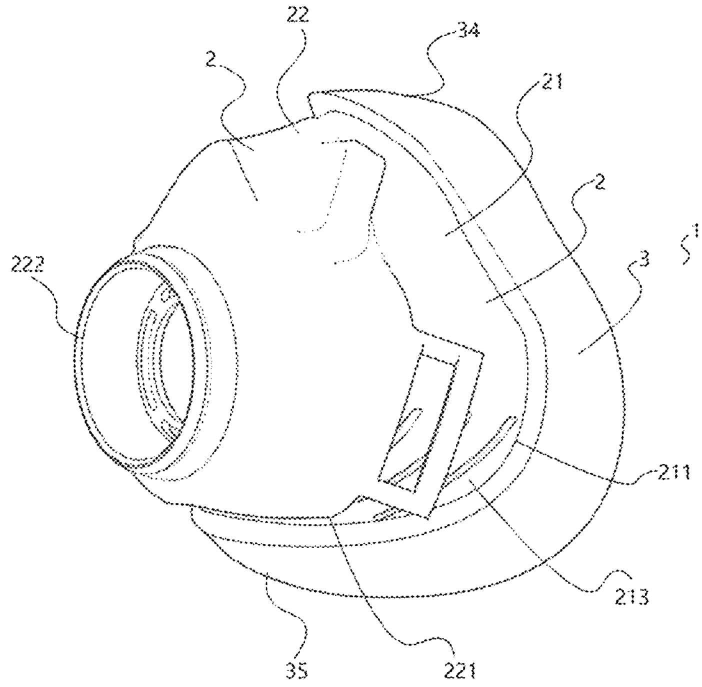
FIG. 3 is a perspective view of the oronasal mask stabilization system according to multiple embodiments of the present disclosure.
Figure 4:
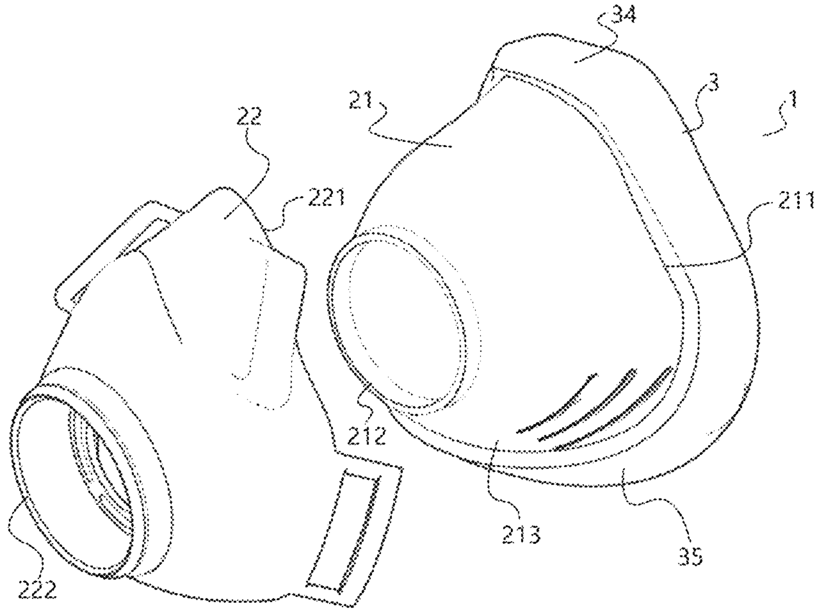
FIG. 4 is an exploded view of the oronasal mask stabilization system according to multiple embodiments of the present disclosure.
Figure 5:
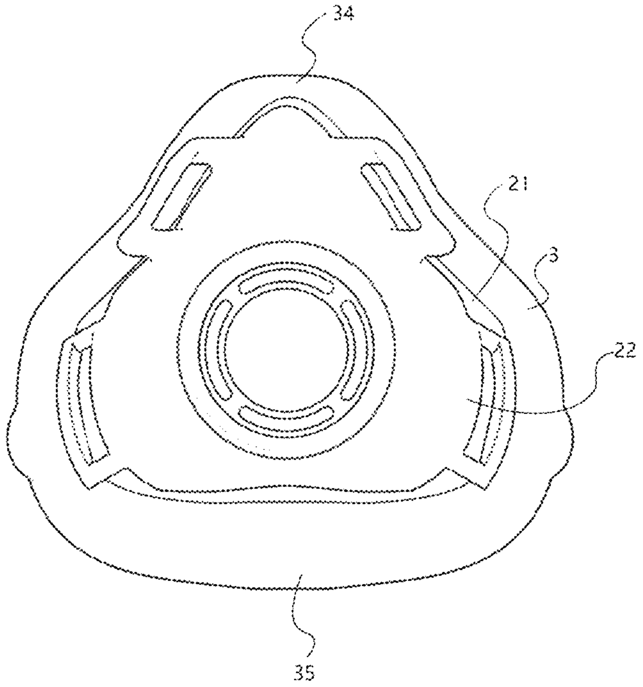
FIG. 5 is a front orthographic view of the oronasal mask stabilization system according to multiple embodiments of the present disclosure.
Figure 6:
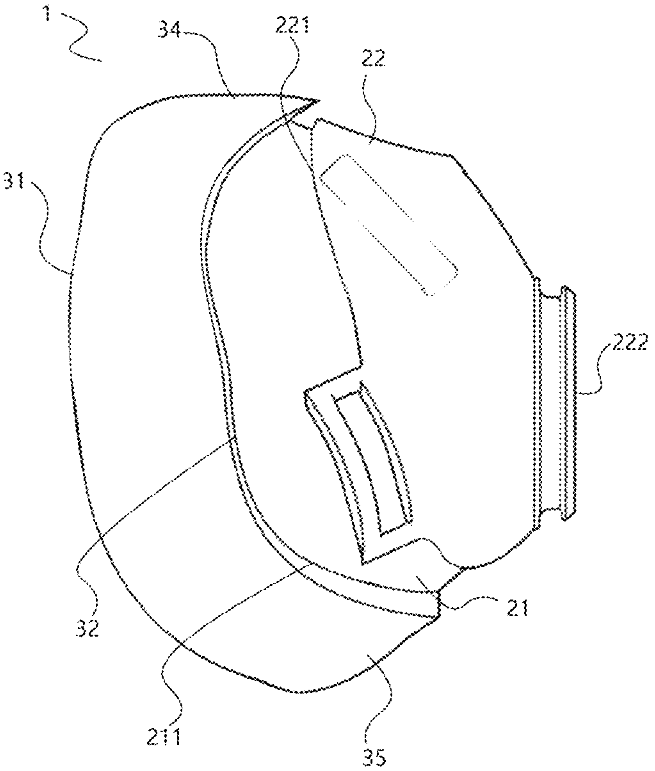
FIG. 6 is a side orthographic view of the oronasal mask stabilization system according to multiple embodiments of the present disclosure.
Figure 7:
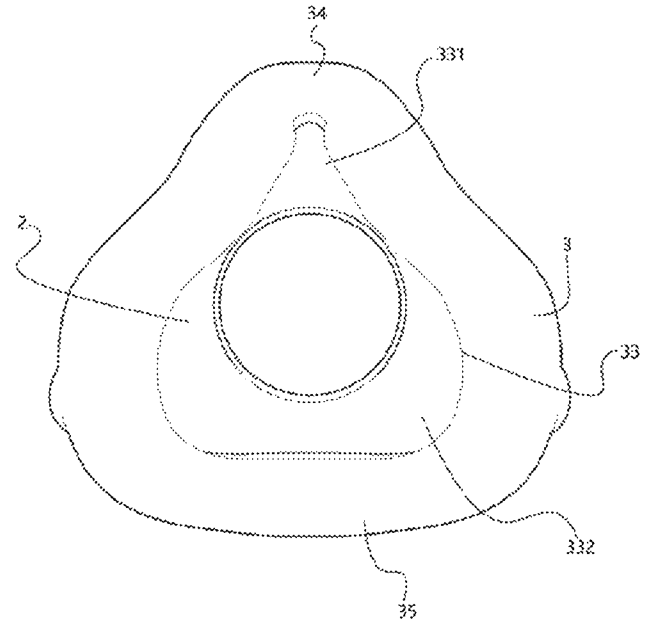
FIG. 7 is a rear orthographic view of the oronasal mask stabilization system according to multiple embodiments of the present disclosure.

This embodiment differs from the Embodiment 1 in that the support member 2 is composed of at least two components. Specifically, the support member 2 includes a main body portion 21 and a mask stabilizer 22, the mask stabilizer 22 being configured to connect with the main body portion 21 in a front-to-back manner (as shown in FIGS. 3 and 4). The main body portion 21 is configured to connect with the sealing formation structure 3 and together form the oronasal mask. The main body portion 21 generally has a hood-shaped structure including a circumferentially extending sidewall 213 with a certain curvature, and is overall constructed to accommodate a pressurized space for airflow. The sidewall 213 is formed at its two ends with a first interface 211 and a second interface 212. The first interface 211 is configured to connect with the sealing formation structure 3, and the second interface 212 is configured to connect with the mask stabilizer 22, an elbow, or other respiratory accessories, thereby forming an air inlet through which positive pressure airflow enters the pressurized chamber. The first interface 211 may be formed with standardized mating dimensions and a sealing groove structure to achieve reliable assembly and airtight connection with the sealing formation structure 3, thereby maintaining morphological stability and sealing performance during long-term use. The second interface 212 may include a curved surface extending toward or away from the pressurized chamber, the curved surface being configured for connection with the mask stabilizer 22, an elbow, or other respiratory accessories. The first interface 211 and the second interface 212 are typically designed as axially symmetric interfaces located at the central left and right sides of the oronasal mask stabilization system 1, and are generally formed as circular openings 33. In some special implementations, the first interface 211 and the second interface 212 may alternatively be designed as elliptical or other shapes according to functional requirements to accommodate interface specifications of different connecting components. The sidewall 213 is integrally formed with a wall thickness of approximately 5 mm, such that while maintaining overall lightweight characteristics, the main body portion 21 is capable of forming a fixed structure and enclosing a pressurized chamber during use. Under normal circumstances, the sidewall 213 is a continuous and uniform solid wall surface, but it may also be provided with a limited number of through-holes or apertures for mounting noise-reduction components as needed for noise suppression, airflow discharge, or functional expansion, allowing exhaust gas exhaled by the patient to be discharged. The sidewall 213 may further include local protrusions or recesses for positioning or securing other respiratory accessories such as the mask stabilizer 22.

In the present embodiment, the main body portion 21 is formed as a rigid or semi-rigid member, which substantially does not undergo elastic deformation during use. It is capable of effectively withstanding multidirectional tensile forces from the headband connection points, thereby reducing deformation-induced sealing failure. By maintaining a fixed geometry, the main body portion 21 provides the oronasal mask stabilization system 1 with a stable pressurized space and airflow passage, ensuring that the mask does not collapse or twist under various wearing conditions, and thus maintaining unobstructed airflow and stable positioning of the sealing region. The material of the main body portion 21 may be selected from biocompatible polymers with high-temperature sterilization resistance, chemical corrosion resistance, and low allergenic properties, such as medical-grade polycarbonate (PC), polypropylene (PP), or polyetheretherketone (PEEK). The surface may undergo treatments such as polishing, anti-fog coating, anti-scratch coating, or skin-friendly coating. Where necessary, antibacterial or antimicrobial coatings may be applied to the surface of the main body portion 21 to inhibit microbial growth. Alternatively, the material may include polyester or polymethyl methacrylate (PMMA, acrylic), which exhibit excellent transparency, impact resistance, and fatigue resistance, or the main body portion 21 may be formed by composite molding of multiple materials so as to balance rigid support, wearing comfort, and aesthetic appearance. The manufacturing method of the main body portion 21 may include, but is not limited to, single-material molding processes such as injection molding, blow molding, or compression molding. It may also be fabricated by multi-material molding processes such as dual-shot injection molding or overmolding. The main body portion 21 is at least partially transparent or semi-transparent to allow visual observation of the patient's face during wearing. In some cases, the main body portion 21 may also be formed as entirely non-transparent.

The joining of the main body portion 21 with the sealing formation structure 3 may include, but is not limited to, an integrally molded unitary structure formed during a single molding process; a detachable connection realized through mechanical mating structures such as snap-fits, slots, or mortise-and-tenon joints; a stable and repeatable assembly achieved by threaded engagement, positioning pins, or locking clasps; a permanent non-detachable bond formed by thermal welding, ultrasonic welding, or laser welding; a flexible connection provided by adhesives, double-sided adhesive tape, or pressure-sensitive adhesive; a direct bond between different materials formed during molding by dual-shot injection molding or overmolding; or a sealing and cushioning interface established by transitional members such as flexible insert rings or sealing gaskets disposed between the main body portion 21 and the sealing formation structure 3.

The mask stabilizer 22 is provided with a third interface 221 and a fourth interface 222 at its two ends, and a continuous wall surface connecting the third interface 221 and the fourth interface 222. The continuous wall surface extends in its longitudinal direction in a hood-shaped configuration and protrudes toward the pressurized chamber to form a cavity. The opening 33 of the third interface 221 is larger in size than the opening 33 of the fourth interface 222. In one case, the fourth interface 222 of the mask stabilizer 22 is connected with the second interface 212 of the main body portion 21. In other cases, the fourth interface 222 is connected with the sidewall 213 of the main body portion 21. The opening 33 of the third interface 221 is smaller than or equal to the opening 33 of the first interface 211. Further limiting this dimensional relationship, preferably, in a front orthographic view, the distance between the third interface 221 and the first interface 211 is less than or equal to 1.5 cm.

Figure 9:
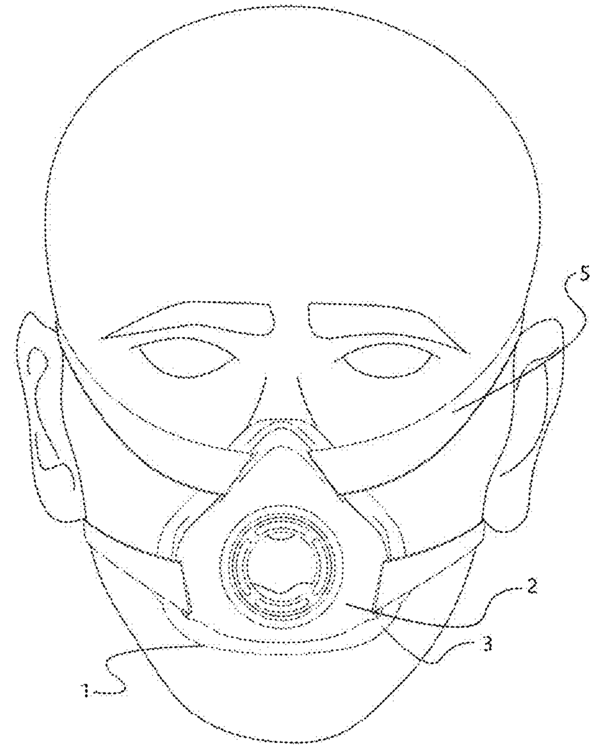
FIG. 9 is a front view of the oronasal mask stabilization system according to multiple embodiments of the present disclosure when worn.
Figure 10:
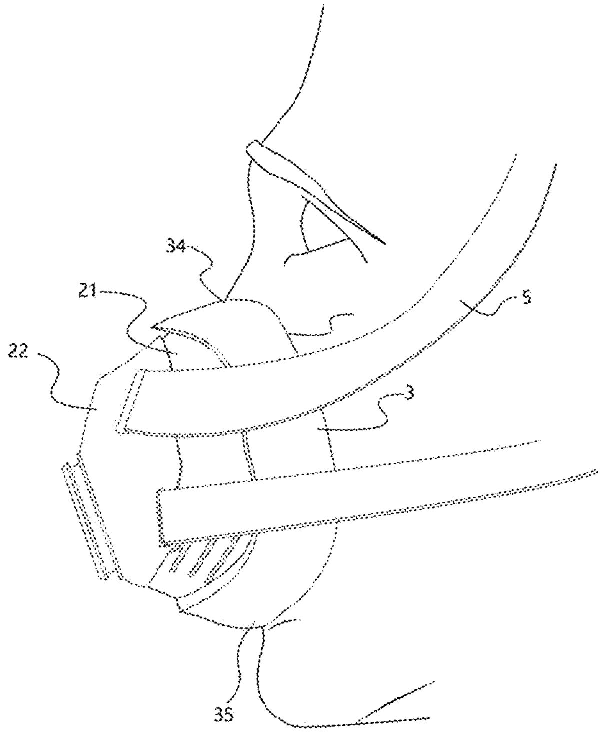
FIG. 10 is a side view of the oronasal mask stabilization system according to multiple embodiments of the present disclosure when worn.
Figure 11:
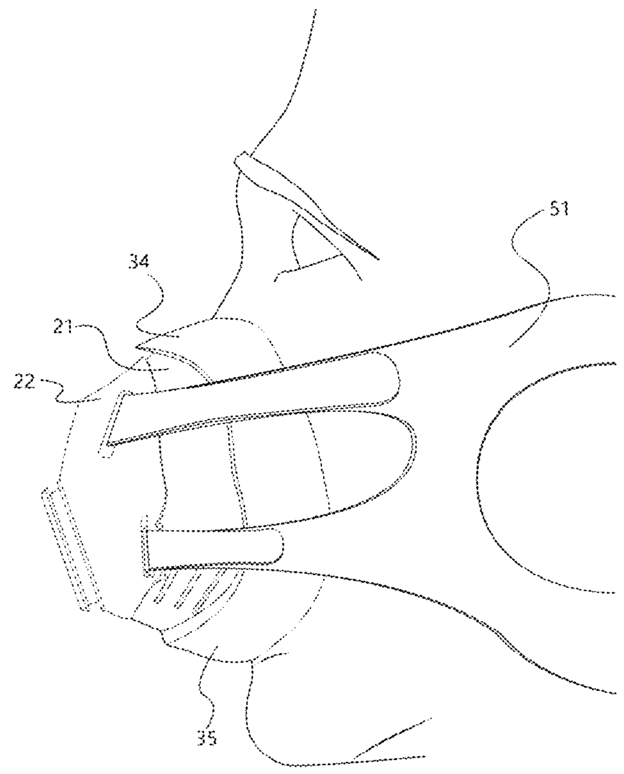
FIG. 11 is a side view of the oronasal mask stabilization system according to multiple embodiments of the present disclosure when worn with a neck strap connected.
Figure 23:
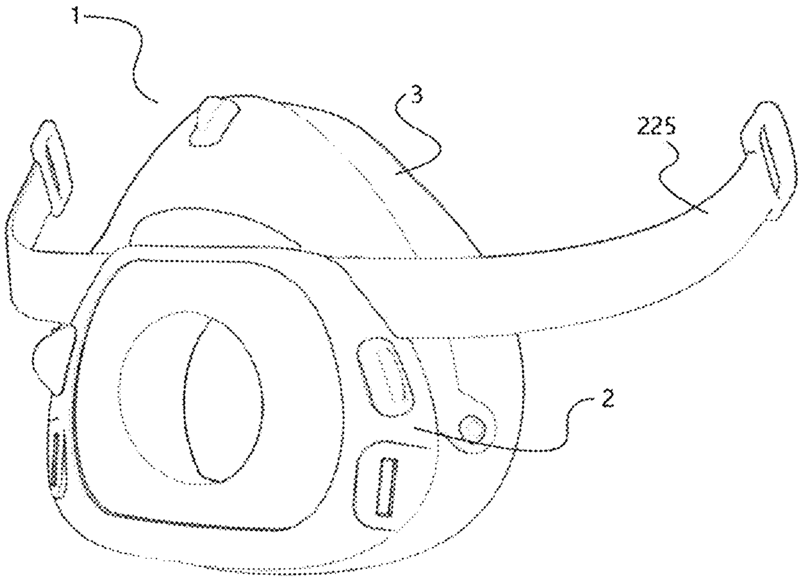
FIG. 23 is a schematic view of the oronasal mask stabilization system with side straps in an embodiment of the present disclosure.

The mask stabilizer 22 is further configured to connect with a fixing assembly 5 so as to achieve stable positioning and reliable fixation of the oronasal mask stabilization system 1 during use. The fixing assembly 5 may include, but is not limited to, a head strap, neck strap, occipital strap, or other adjustable tensile band, as well as additional connection structures configured to adjust length, tension, or angle (as shown in FIGS. 9 and 10). The fixing assembly 5 is securely coupled to the mask stabilizer 22 through its interfaces or dedicated connecting structures, thereby providing multidirectional tensile support for the oronasal mask stabilization system 1. This enables the mask to remain closely fitted to the patient's face during wearing while preventing displacement or air leakage caused by body movement or repositioning. In some cases, the connection between the mask stabilizer 22 and the fixing assembly 5 may be a detachable connection, for example, achieved by snap-fit, pin, threaded, or magnetic interfaces, thereby facilitating mask disassembly, cleaning, maintenance, or replacement of the fixing assembly 5. In such cases, the mask stabilizer 22 is provided with connecting structures configured to engage with the fixing assembly 5. The connecting structures may include, but are not limited to, at least one opening formed in the wall surface of the mask stabilizer 22, the opening being adapted for insertion, fastening, or engagement of the fixing assembly 5, such as a head strap, adjustment strap, or other accessory for securing the mask stabilization system to the patient's face. Alternatively, the mask stabilizer 22 may cooperate with a secondary connecting member to form a connection to the fixing assembly 5. In some cases, the mask stabilizer 22 includes a side strap 225, the side strap 225 being configured to extend from the main body of the mask stabilizer 22 and to cooperate with the fixing assembly 5 to achieve stable fixation of the mask on the patient's face (as shown in FIG. 23). The side strap 225 may be formed of a material different from that of the mask stabilizer 22, and may be made of a material more flexible than that of the mask stabilizer 22 so as to enhance comfort and adaptability to deformation during wearing. The connection between the side strap 225 and the mask stabilizer 22 may include a mechanical snap-fit, insertion structure, threaded connection, riveting, adhesion, thermal welding, or ultrasonic welding. In some embodiments, the side strap 225 and the mask stabilizer 22 may be integrally molded as a unitary structure to ensure connection stability and long-term durability. In the present embodiment, the side strap 225 is connected to the mask stabilizer 22 by a detachable slot or snap-fit, allowing the patient to adjust tightness according to head size and wearing requirements, thereby balancing fixation stability and comfort. Furthermore, the arrangement and connection of the side strap 225 may vary, including single-sided or double-sided extension, or being formed in an annular, U-shaped, or other curved configuration to optimize force distribution and improve wearing comfort and sealing performance. In other cases, the connection may be a non-detachable fixation, such as welding, adhesion, ultrasonic fusion, or thermal fusion, so as to enhance the overall structural stability. In the present disclosure, the fixing assembly 5 may further include a novel neck strap 51, which is configured to provide stable support and positioning of the oronasal mask stabilization system 1 without extending over the patient's cranium, but instead by surrounding the patient's neck or fitting against the posterior head region near the base of the neck (as shown in FIG. 11). This configuration is intended to address issues commonly associated with conventional head-strap fixation methods, such as discomfort during wearing, pressure on the top of the head, and interference with hairstyles.

Figure 12:
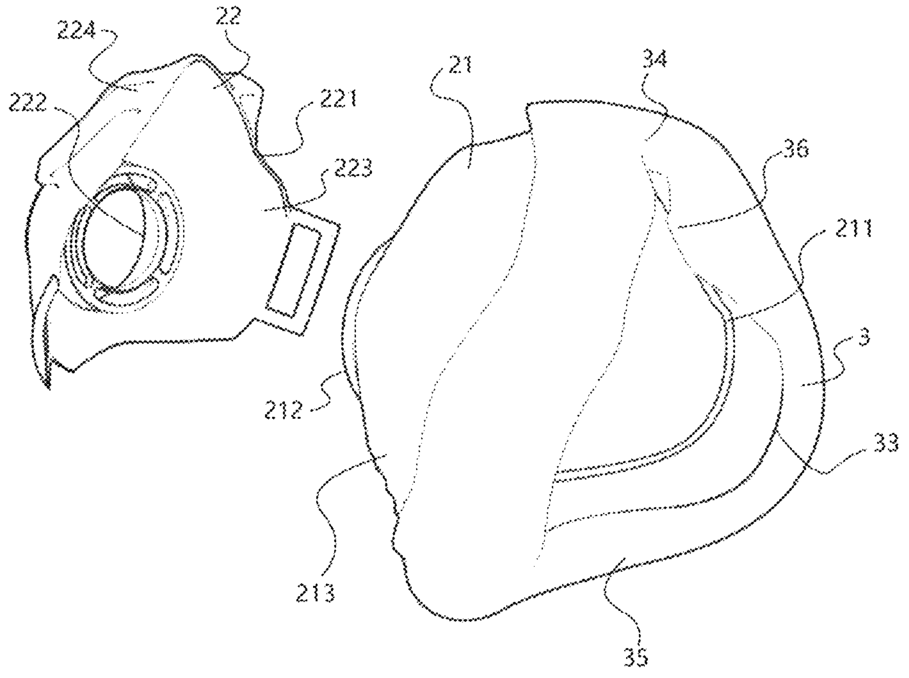
FIG. 12 is a schematic view illustrating a connection between a main body portion and a mask stabilizer according to multiple embodiments of the present disclosure.

The mask stabilizer 22 and the main body portion 21 may be separable, and the mask stabilizer 22 is connected to the main body portion 21 through mutually conforming shapes, for example, by means of similar or closely matching contour geometries. In one implementation, the mask stabilizer 22 is configured to be connected to the main body portion 21 in a front-to-back manner. The continuous wall surface connecting the third interface 221 and the fourth interface 222 includes an inner wall 223 and an outer wall 224 disposed opposite to each other. The inner wall 223 is the wall surface on the inside of the hood-shaped structure, its geometry being configured to at least partially contact or fit against the corresponding hood-shaped structure of the main body portion 21 when the oronasal mask stabilization system 1 is assembled, thereby achieving structural positioning and support (as shown in FIG. 12). The outer wall 224 is located on the outside of the hood-shaped structure and may be designed as a smooth curved surface or with protrusions, recesses, or other surface features according to functional requirements. Typically, the inner wall 223 and the outer wall 224 may have a uniform or gradient wall thickness distribution so as to balance strength, weight, and compliance. The hood-shaped structure of the mask stabilizer 22 and the hood-shaped structure of the main body portion 21 are at least partially consistent in curvature, thereby ensuring accurate alignment and stable engagement during assembly. In certain implementations, the curvatures may be completely matched to achieve full-contact engagement, or only partially matched to form localized gaps, thereby accommodating different sealing performance and airflow regulation requirements. The mask stabilizer 22 may be fixedly or detachably connected with the main body portion 21 by various means such as mechanical snap-fit, threaded connection, slot engagement, welding, adhesion, or ultrasonic fusion, in order to meet different maintenance, cleaning, and replacement requirements. With respect to materials, the mask stabilizer 22 is preferably made of high-rigidity, fatigue-resistant, and impact-resistant materials, such as polycarbonate (PC), polyetheretherketone (PEEK), polyamide (PA) reinforced composites, or metallic alloys, so as to maintain structural stability under long-term loading and repeated sterilization conditions. In some implementations, the outer wall 224 may further be provided with a surface treatment such as an anti-slip coating to enhance functionality and improve wearing comfort.

Figure 21:
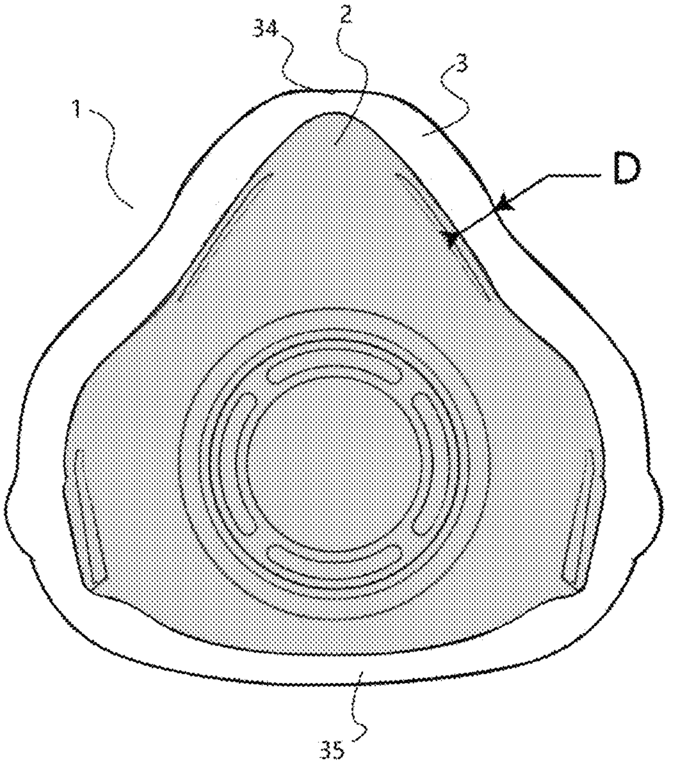
FIG. 21 is a schematic view illustrating a coverage of a positioning stabilizer in an embodiment of the present disclosure.
Figure 22:
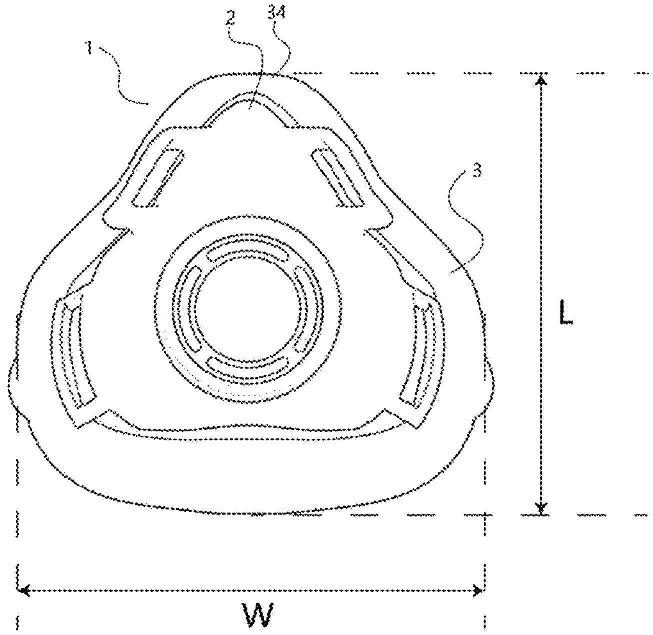
FIG. 22 is a schematic view illustrating a length and width of the oronasal mask stabilization system in an embodiment of the present disclosure.

In addition to optimizing and improving the structure of the oronasal mask stabilization system 1, the present disclosure further specifies clear numerical requirements for key parameters of the oronasal mask stabilization system 1. In particular, for a medium-sized oronasal mask stabilization system 1, in a front orthographic view, the maximum distance between the outer contour of the mask stabilizer 22 and the outer contour of the sealing formation structure 3 is less than or equal to 3 mm (as shown in FIG. 21, where D≤3 mm). This design ensures that the mask stabilizer 22 closely conforms to the peripheral contour of the main body portion 21 while maintaining overall compactness without interference or friction, thereby effectively reducing shaking or displacement of the mask during wearing and improving both stability and sealing performance. In addition, this close arrangement facilitates cooperative interaction between the mask and the fixing assembly 5, resulting in more uniform force transmission during wearing, avoiding localized pressure concentration, and thereby enhancing wearing comfort and improving long-term compliance. Furthermore, the length of the oronasal mask stabilization system 1 is defined to be in the range of 3 cm to 10.5 cm, with the aspect ratio of width to length further limited to not exceed 1.5 (as shown in FIG. 22, illustrating the length and width of the oronasal mask stabilization system 1). When the mask stabilizer 22 of the support member 2 is configured without the side strap 225, this dimensional ratio ensures that the mask contour remains compact while adequately covering both the nasal and oral airways of the patient, thereby reducing discomfort or pressure caused by excessive lateral expansion and simultaneously improving stability and sealing performance during wearing. It also prevents instability of the airflow passage and discomfort associated with excessive width or length of the mask, thus enhancing long-term compliance and therapeutic effectiveness.

Embodiment 3

In this embodiment, an oronasal mask stabilization system 1 is provided. The oronasal mask stabilization system 1 includes: a support member 2 configured to have a curvature at least partially facing the patient; and a sealing formation structure 3 configured to be connected to the support member 2 and to seal against the patient's face. The sealing formation structure 3 is constructed to have a top portion 34 and a bottom portion 35. The top portion 34 is configured to contact the nasal root of the patient during use and to form a seal below the nasal bridge and above the nasal tip. The bottom portion 35 is configured to contact and seal against the mandibular region of the patient. The sealing formation structure 3 has a first side 31 configured to contact the patient's face, and a second side 32 configured to be connected to the support member 2. The first side 31 comprises at least one opening 33, the at least one opening 33 including a nasal receiving region 331 and an oral receiving region 332. The nasal receiving region 331 at least accommodates the nasal tip and alar portions of the patient's nose. Furthermore, the nasal receiving region 331 includes flaps 36 distributed on the left and right sides thereof, the flaps 36 being configured to fit against the nasal alae of the patient during use.

Figure 27:
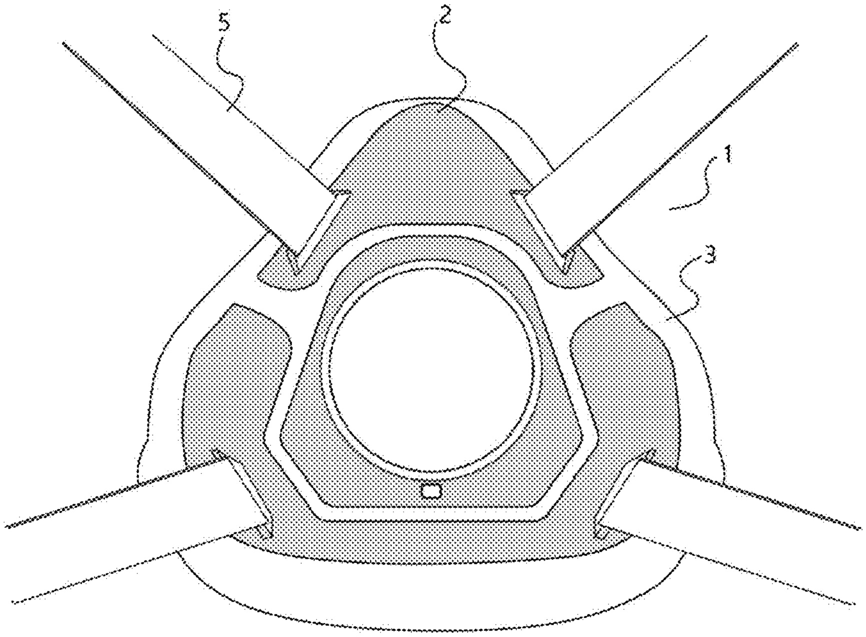
FIG. 27 is a schematic view of a support member having a composite structure combining a rigid member and a flexible member in an embodiment of the present disclosure.
Figure 28:
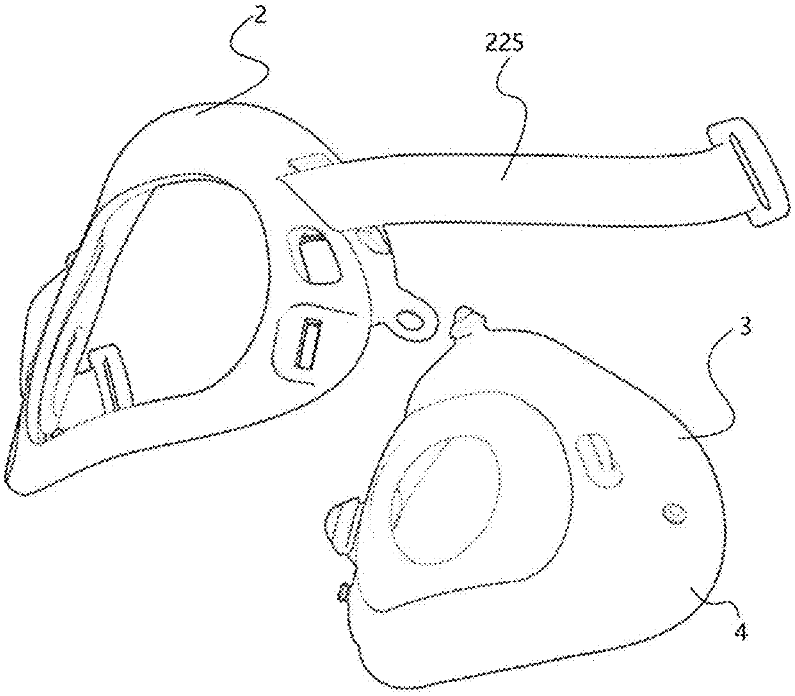
FIG. 28 is a schematic view illustrating the flexible member and the rigid member of the support member are manufactured independently as separate components in an embodiment of the present disclosure.
Figure 29:
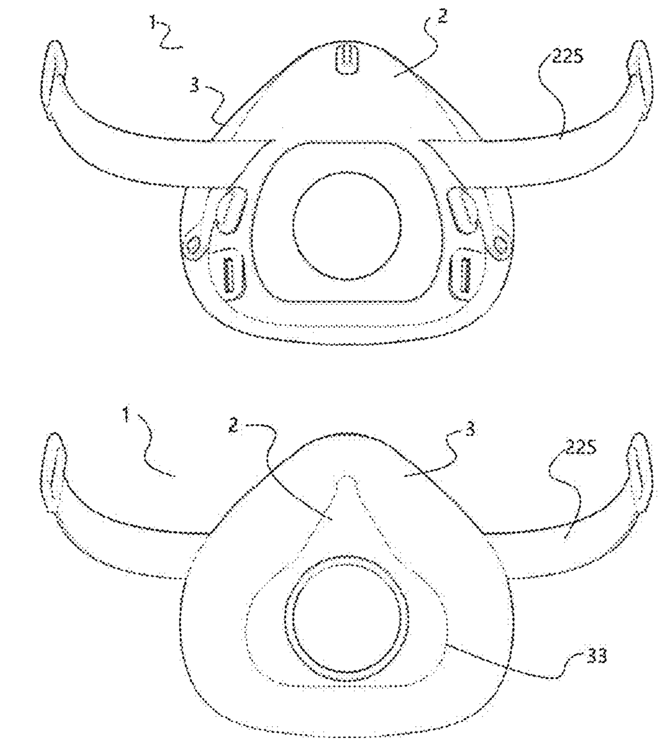
FIG. 29 is a schematic view illustrating the flexible member and the rigid member of the support member are manufactured independently and then assembled and connected in an embodiment of the present disclosure.
Figure 30:
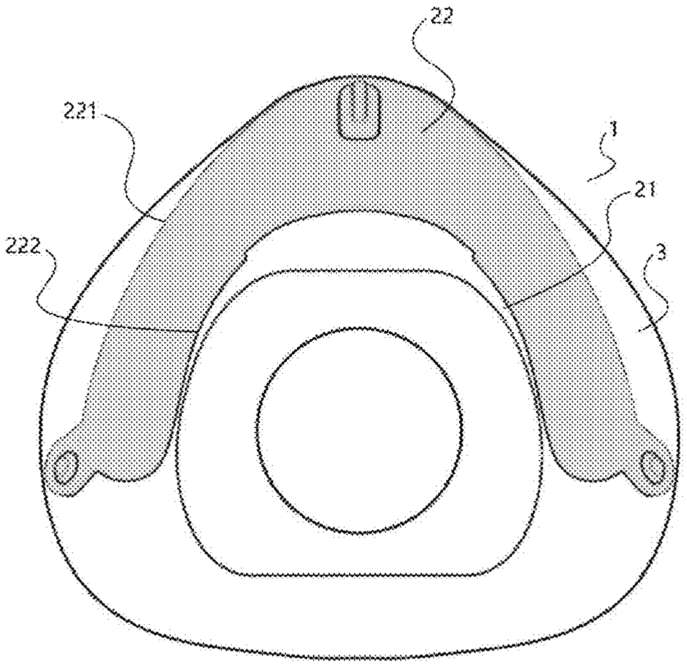
FIG. 30 is a schematic view of the mask stabilizer and the main body portion being non-detachable in an embodiment of the present disclosure.

This embodiment differs from Embodiment 1 in that, as shown in FIGS. 27 to 31, the support member 2 is at least partially a flexible component. The main body is formed as a combination of flexible and rigid members, and such combination may be realized in at least two manners, namely an integrally formed structure and an assembled structure. In the first case, the support member 2 is constructed such that rigid and flexible components together form a continuous wall surface, different regions of the same wall surface being made of materials with different mechanical properties. Since the main body portion 21 and the mask stabilizer 22 together form one assembly, the main body portion 21 may be understood as a combination of rigid and flexible components, i.e., the main body portion 21 is at least partially flexible and at least partially rigid or semi-rigid. The flexible component divides the rigid member into a plurality of independent supporting zones (as shown in FIG. 27, which may include upper and lower zones or more). Each supporting zone corresponds to a different point of tensile load (for example, the four force-bearing points where the mask connects to the fixing assembly 5 such as a head strap), and the supporting zones are mechanically independent so as to prevent localized loading from propagating deformation throughout the entire structure. The rigid members provide the necessary structural strength, shape retention, and stability of the airflow passage, while the flexible components impart moderate deformability and conformability between zones, especially in areas in direct contact with the patient's face, thereby alleviating localized pressure and improving comfort. When the head strap applies tensile forces at four connection points in different directions, conventional fully rigid main body structures often experience overall displacement or localized lifting due to load coupling, resulting in sealing failure and air leakage. In the present design, however, the rigid zones are separated by flexible materials such that the forces at each point are effectively isolated, allowing the tensile force to act only on the targeted zone without interfering with other regions, thereby significantly reducing the risk of displacement caused by uneven loading. This partitioned mechanical structure achieves a balance among sealing performance, structural stability, and wearing comfort. Furthermore, the ratio of rigid to flexible portions may be adjusted to accommodate diverse application requirements. During manufacturing, flexible and rigid materials may be directly combined within the same mold by multi-material injection molding, secondary injection molding, or co-molding processes to form a seamless integrated structure. In the second case, the flexible component and the rigid member are manufactured separately and then fixed together by means such as mechanical snap-fit, threaded engagement, insertion coupling, adhesive bonding, or ultrasonic welding, thereby ensuring airtightness while facilitating subsequent disassembly, replacement, or maintenance (as shown in FIGS. 28 and 29). In such implementations, the main body portion 21 is at least partially flexible component, while the mask stabilizer 22 is at least partially rigid member. Preferably, the main body portion 21 is formed of flexible component to ensure sufficient compliance in the facial sealing region for alleviating pressure and adapting to different facial contours, and the mask stabilizer 22 is formed of rigid member to withstand tensile forces from the fixing assembly 5 (e.g., head straps) and to maintain shape and positional stability of the mask during use. Furthermore, this flexible-rigid separable and re-assemblable design may be extended into a modular structure. In other cases, the mask stabilizer 22 and the main body portion 21 may be inseparable (as shown in FIG. 30), the main body portion 21 and the sealing formation structure 3 together form the mask, and the mask stabilizer 22 is connected to the main body portion 21. The connection may be achieved by various means including, but not limited to, industrial adhesive bonding, hot melt bonding, structural adhesive chemical bonding, ultrasonic welding, laser welding, thermal pressing, high-frequency welding, or in-mold overmolding. In some implementations, the mask stabilizer 22 and the main body portion 21 may also be detachable. Additionally, the exterior of the mask stabilizer 22 may be overmolded to form a soft covering layer. This covering layer provides auxiliary cushioning between the mask and the patient's face, thereby further enhancing sealing performance and wearing comfort. Moreover, the covering layer can serve protective and wear-resistant functions, extending the service life of the product and improving its stability and reliability during long-term use.

Figure 31:
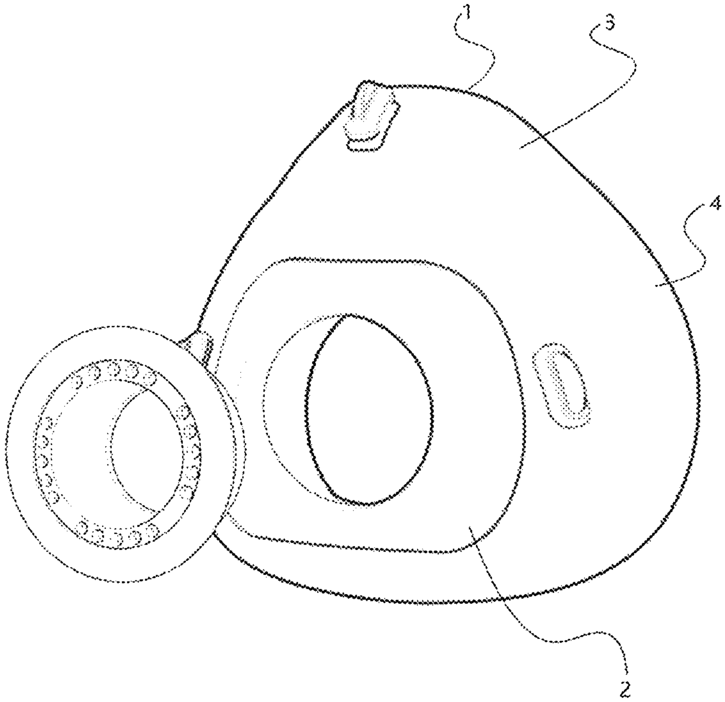
FIG. 31 is a schematic view of the support member entirely formed of the flexible member in an embodiment of the present disclosure.

In other implementations, the support member 2 is entirely formed of a flexible component (as shown in FIG. 31). This design allows the support member 2 to accommodate minor variations in different facial contours during wearing and to achieve stable support and precise conformity with the sealing formation structure 3 through its own deformation. In the absence of a rigid framework, the flexible support member 2 can effectively absorb impact in the event of accidental collision or external force, thereby reducing the risk of facial injury to the patient, while also significantly alleviating pressure on the skin and soft tissues during wearing, thus improving comfort for long-term use. In addition, the flexible structure can be folded, rolled, or compressed within a certain range, which facilitates storage and portability, while maintaining stable geometry and airtight performance even after repeated deformation. From a manufacturing perspective, the fully flexible support member 2 may be produced by one-step molding processes such as compression molding, injection molding, extrusion, or 3D printing. Structurally, reinforcement ribs, gradient-thickness regions, or multi-cavity cushioning structures may be integrated to enhance overall stability and durability. Furthermore, the flexible support member 2 may be combined with flexible materials of different hardness levels in a zoned configuration, thereby achieving a functional distribution of locally softer and locally more supportive regions, and thus attaining an optimal balance between support and comfort.

Embodiment 4

In this embodiment, an oronasal mask stabilization system 1 is provided. The oronasal mask stabilization system 1 includes: a support member 2 configured to have a curvature at least partially facing the patient; and a sealing formation structure 3 configured to be connected to the support member 2 and to seal against the patient's face. The sealing formation structure 3 is constructed to have a top portion 34 and a bottom portion 35. The top portion 34 is configured to contact the nasal bridge of the patient during use and to form a seal below the nasal root and above the nasal tip. The bottom portion 35 is configured to contact and seal against the mandibular region of the patient. The sealing formation structure 3 has a first side 31 configured to contact the patient's face, and a second side 32 configured to be connected to the support member 2. The first side 31 comprises at least one opening 33, the at least one opening 33 including a nasal receiving region 331 and an oral receiving region 332. The nasal receiving region 331 at least accommodates the nasal tip and alar portions of the patient's nose. Furthermore, the nasal receiving region 331 includes flaps 36 distributed on the left and right sides thereof, the flaps 36 being configured to fit against the nasal alae of the patient during use.

Figure 32:
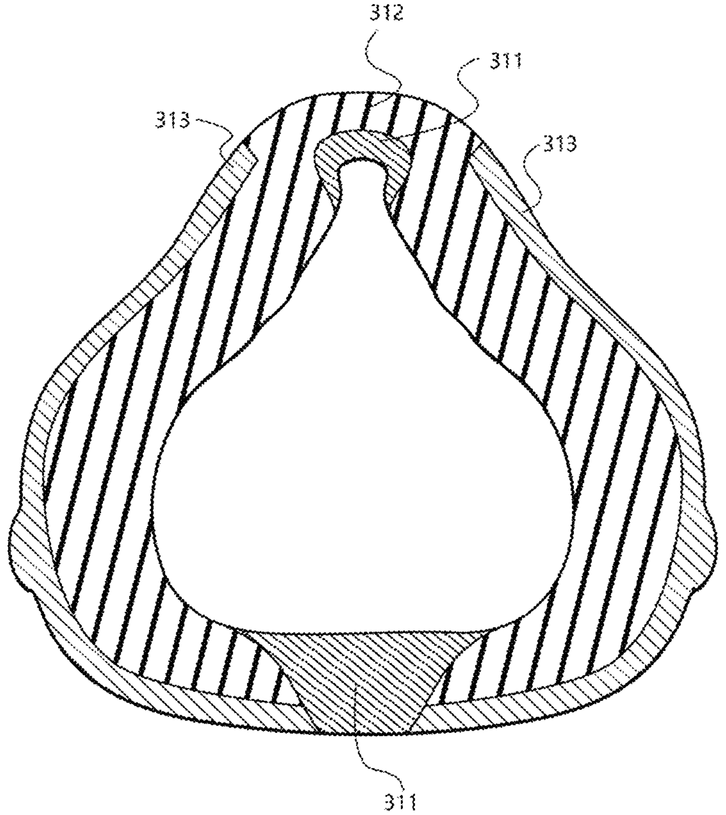
FIG. 32 is a rear view of the sealing formation structure divided into at least three regions of different thicknesses in an embodiment of the present disclosure.
Figure 33:
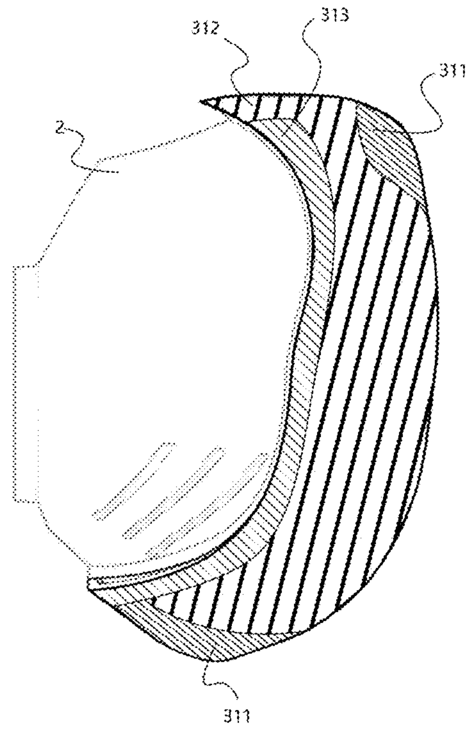
FIG. 33 is a side view of the sealing formation structure divided into at least three regions of different thicknesses in an embodiment of the present disclosure.
Figure 34:
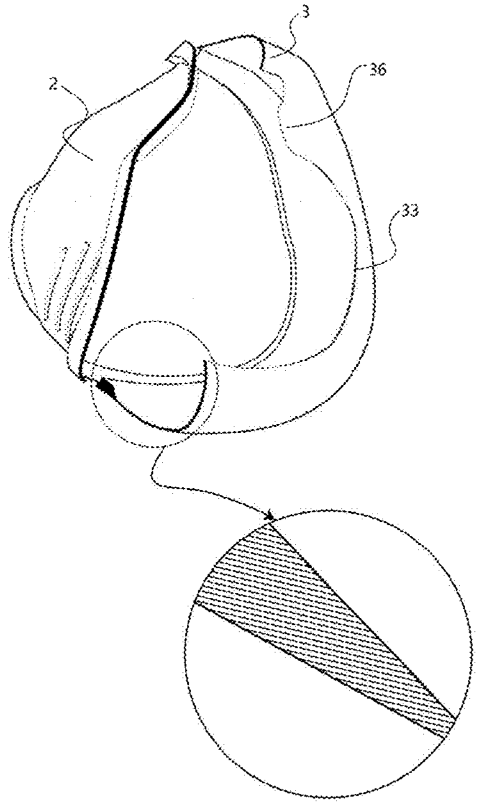
FIG. 34 is a schematic view of the sealing formation structure being at least partially configured with a gradient wall thickness in an embodiment of the present disclosure.
Figure 35:
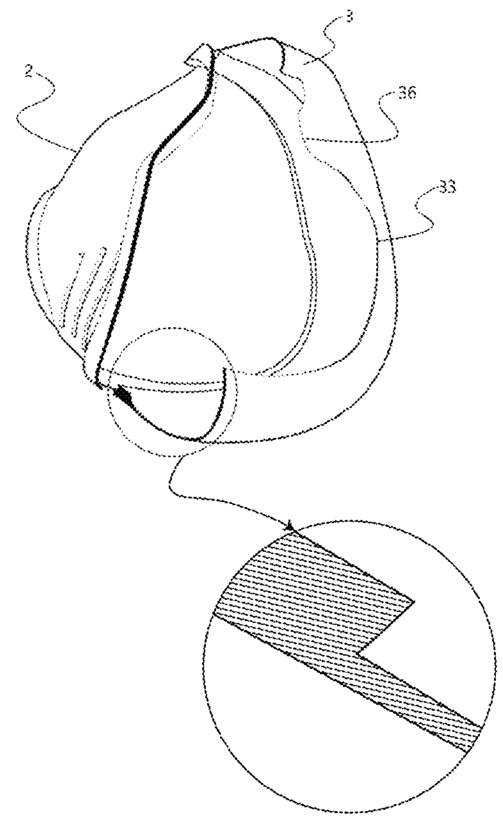
FIG. 35 is a schematic view of the sealing formation structure being at least partially configured with an abrupt change in wall thickness in an embodiment of the present disclosure.

This embodiment differs from the Embodiment 1 in that the sealing formation structure 3 may include different thickness zones, and in the present embodiment the sealing formation structure 3 is divided into at least three regions of different thicknesses. Specifically, these include a thin region 311 located at the top portion 34 and the bottom portion 35; an thick region 312 positioned between the first side 31 and the second side 32; and a thickest region 313 located between the thick region 312 and the second side 32 (as shown in FIGS. 32 and 33). This division provides clear functional and technical purposes. The thin region 311 of the top portion 34 and the bottom portion 35, designed as a thin-wall structure, is primarily configured to closely conform to the patient's facial contours, particularly at sensitive areas such as above the nasal bridge and beneath the mandible, thereby allowing the mask to undergo moderate deformation during wearing and breathing. This reduces localized pressure and improves long-term comfort. In some cases, the thin region 311 may further include the edge portions located on either side of the opening 33. The thick region 312, disposed between the first side 31 and the second side 32 and contacting the patient's cheeks during use, provides sufficient structural support through increased wall thickness, ensuring that the mask maintains a stable sealing surface under lateral tensile forces or pressure variations and preventing sealing failure. Typically, the thin region 311 has a uniform wall thickness, which helps maintain sealing stability, reduce fluctuations in airtightness caused by uneven thickness, and prevent localized leakage, thereby ensuring reliable conformity of the oronasal mask stabilization system 1 with the patient's face during long-term use. The thick region 312 also generally has a uniform wall thickness, which provides stable structural support and shape retention while ensuring uniform loading when in contact with the patient's face. In some cases, however, the sealing formation structure 3 may be partially formed with a gradient wall thickness (as shown in FIG. 34), where the wall thickness gradually changes along a specific direction or region. The thickest region 313, located between the thick region 312 and the second side 32, is significantly thicker than the thick region 312. This region functions as a load-bearing and supporting portion, preventing overall displacement or rolling of the sealing formation structure 3 caused by high internal pressure or tensile forces from the head strap. The thickest region 313 also serves as a stable base for connection with the main body portion 21, thereby ensuring secure attachment of the sealing formation structure 3 to the mask body. Overall, this zoning design achieves a balance between flexible conformity and structural stability, enabling the mask to provide reliable airtightness while maintaining comfort and durability during long-term use. The different thickness regions may be realized either through gradient transitions in wall thickness or through abrupt thickness changes (as shown in FIG. 35). In one implementation, the sealing formation structure 3 may at least partially include abrupt changes in wall thickness. A gradient thickness design helps reduce the effect of sudden rigidity transitions on wearing comfort and lowers the risk of stress concentration at the seal, whereas an abrupt thickness design enables clearer functional differentiation among regions. Furthermore, the surfaces of the different thickness regions may undergo differentiated texturing treatments, such as smooth surfaces in the thin region 311 to reduce friction, and micro-protrusions or corrugations in the thick region 312 to enhance anti-slip properties and conformity. Such arrangements achieve a dual optimization of structural function and wearing experience.

Figure 36:
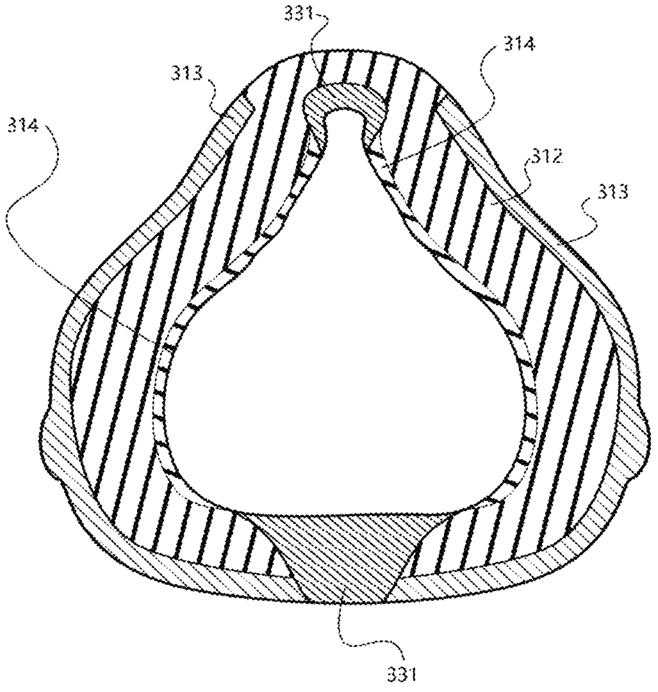
FIG. 36 is a rear view of the sealing formation structure divided into at least four regions of different thicknesses in an embodiment of the present disclosure.

In other implementations, the sealing formation structure 3 is divided into at least four regions of different thicknesses. Specifically, these include a thin region 311 located at the top portion 34 and the bottom portion 35; a thick region 312 located in the intermediate area of the sealing formation structure 3 between the first side 31 and the second side 32 and configured to contact the cheeks during use; a thickest region 313 located between the thick region 312 and the second side 32; and a thicker region 314 located at the edge of the opening 33 and not belonging to the thin region 311, the thicker region 314 having a thickness greater than that of the thick region 312 (as shown in FIG. 36). Based on the three-zone division, the addition of the thicker region 314 primarily enhances the stability and deformation resistance of the edge of the opening 33 so as to maintain the integrity of the opening 33 configuration. This prevents sealing failure caused by external force or tensile stress applied to the edge of the opening 33 during wearing, thereby further improving the wearing comfort, sealing performance, and long-term reliability of the oronasal mask stabilization system 1.

The oronasal mask stabilization system 1 of the present disclosure provides at least the following beneficial effects:

1. The oronasal mask stabilization system 1 of the present disclosure achieves an overall lightweight design through structural optimization and material reduction, without compromising sealing performance or supporting strength. This configuration significantly reduces compressive load on facial soft tissues, bony prominences such as the nasal bridge, and other facial areas during wearing. The lightweight nature of the oronasal mask stabilization system 1 not only alleviates fatigue and discomfort caused by prolonged use, but also decreases the risk of pressure-related skin complications, including pressure marks, erythema, and pressure ulcers, thereby making it particularly suitable for patients with respiratory diseases requiring long-term continuous positive airway pressure therapy. Furthermore, by positioning the sealing point at the mid-portion of the nasal bridge rather than at the nasal root as in conventional systems, the present disclosure avoids obstruction of the infraorbital region, expands the wearer's horizontal and vertical fields of view, and improves convenience during use. This design allows wearers to perform daily activities such as reading, walking, and communicating with an enhanced visual experience, thereby increasing overall comfort and usability. Consequently, the optimized design renders the mask more suitable for continuous wearing across multiple time periods and scenarios in both clinical and home applications, offering improved ergonomic adaptability and patient compliance.
2. During the development process, curvature control of the top portion 34 constituted an important and highly challenging technical difficulty, particularly in view of the long-standing problem in the prior art wherein prolonged wearing of masks often results in visible facial indentations and discomfort. In the present disclosure, the top portion 34 of the sealing formation structure 3 was subjected to a highly optimized design. This improvement was not a mere geometric adjustment, but rather a systematic innovation directed to multiple technical requirements, including sealing stability during long-term wearing, facial comfort, and material contact sensation at this critical region. The top portion 34 is the location where the mask directly contacts and seals a sensitive part of the face, where the skin is relatively thin and sealing relies largely on the mask itself. In practice, determination of the curvature of the top portion 34 required consideration not only of geometric conformity with the facial contour, but also of the airflow sealing pathway, the deformation characteristics of the material under varying environmental temperature and humidity, and the rebound stability of the material after prolonged loading. Within a reasonable range, the sealing surface of the top portion 34 was extended and its inclination angle precisely adjusted, combined with multiple iterations and fine-tuning of micro-parameters. This process was supported by large-sample data collection and analysis across different populations, genders, and age groups. Each minor adjustment of curvature was verified through repeated wearing trials, sealing performance evaluations, and skin pressure distribution tests, consuming significant time and experimental resources. After hundreds, and in some cases thousands, of comparisons and validations of micro-variations, an optimal balance was ultimately achieved in the extension length, inclination angle, and local curvature of the top portion 34. This breakthrough effectively resolved the technical bottleneck commonly encountered in existing commercial masks, namely the formation of facial indentations and reduced comfort during prolonged use, and it established a marked performance distinction from existing products in terms of patient compliance and user experience, thereby delivering a qualitative improvement in technical effect.
3. Sealing performance is one of the core functional characteristics of the oronasal mask stabilization system 1, as it directly determines the airflow delivery efficiency of positive airway pressure therapy, treatment stability, and patient compliance. In the present disclosure, the sealing point is optimized and positioned in the mid-region of the nasal bridge. Compared with conventional designs where the sealing point is located at the nasal root, the placement at the middle of nasal bridge avoids the infraorbital margin and nasal bone protrusion, where the skin covering is extremely thin and the contour transitions are sharp, which are high-stress regions prone to leakage or discomfort. By contrast, placement at the mid-nasal bridge provides a more continuous and stable contact surface, thereby effectively reducing the risk of localized lifting or leakage caused by uneven facial topography. Compared with designs where the sealing point is located at the nasal tip, the mid-nasal bridge strategy further provides advantages, as the nasal tip is a dynamic region with highly elastic and variable soft tissue, making it difficult to achieve a stable seal and prone to frequent leakage, pressure-induced pain, or skin damage. The mid-nasal root region, on the other hand, has relatively thicker and more stable soft tissue that is less likely to shift due to facial expressions or sleeping posture, and therefore provides higher structural tolerance and prolonged sealing conformity. Accordingly, the sealing strategy of the present disclosure, which locates the sealing point at the mid-nasal root region, demonstrates significant advantages in terms of structural stability, anatomical adaptability, and airtightness maintenance, thereby serving as a critical guarantee for achieving efficient, comfortable, and long-term positive airway pressure support.

4. The present disclosure addresses the limitations of conventional oronasal mask stabilization systems 1 with respect to structural stability and supporting performance by implementing systematic structural optimization and functional improvements. By redesigning the layout of the sealing structure, adjusting the position and dimensional proportions of the supporting framework, and introducing ergonomically refined component configurations, the overall system achieves significantly improved stability and balanced support during wearing while maintaining sealing performance. On the basis of the improved oronasal mask stabilization system 1, the present disclosure further introduces an optimized mask stabilizer 22 adapted thereto. Compared with existing market products, this mask stabilizer 22 is positioned closer to the edge of the oronasal mask stabilization system 1 and, while appropriately sized, provides an increased coverage area. The optimized structure enables more effective distribution of mask weight and counterforce generated by ventilation across the central facial region, thereby avoiding excessive localized load at pressure points and reducing stress concentration on bony prominences of the face. As a result, wearer discomfort and the risk of pressure injuries during long-term use are alleviated. Moreover, the improved supporting system exhibits enhanced geometric stability, maintaining reliable conformity even during changes in patient posture, speech movements, or mild facial expressions. This reduces the likelihood of displacement or leakage, and markedly enhances the dynamic adaptability and clinical applicability of the product. Such a structural design not only improves safety and comfort during use, but also provides a more reliable supporting foundation for extended wearing across multiple scenarios.
5. The oronasal mask stabilization system 1 provided by the present disclosure is capable of accommodating a wide variety of facial morphologies, including but not limited to populations with differences in nasal bridge height, nasal alae width, and facial prominences, and it provides distinct advantages for individuals with a low nasal root or flat nose. In response to variations in facial structure, the present disclosure effectively avoids the conformity issues caused by differences in nasal root height and nasal alae size, thereby ensuring reliable sealing conformity and airtightness across different races and patient groups. In addition, for individuals with congenital craniofacial abnormalities, the oronasal mask stabilization system 1 of the present disclosure is designed to avoid regions of significant structural variation, thereby further enhancing racial adaptability and sealing conformity. Furthermore, the flap structures 36 described herein demonstrate excellent adaptability. By incorporating flexible, adjustable materials and structural arrangements into the design of the flaps 36, these components provide both reliable airtight sealing and stable supporting force, while accommodating individual differences in facial width, high cheekbones, or deep facial depressions. This design markedly improves both comfort and stability of the mask during prolonged use.
6. The oronasal mask stabilization system 1 of the present disclosure significantly improves patient handling efficiency. The system may also be used in combination with a neck strap structure as an optimization over conventional headband-based fixation, thereby providing structural, ergonomic, and experiential advantages. Compared with traditional headband wearing, the neck strap structure transfers the supporting points of the mask or associated components from the head to the neck region, thereby markedly reducing head pressure and wearing burden while improving comfort and stability. This configuration is particularly suitable for elderly patients, patients with head sensitivity, and those requiring long-term use during nighttime. Conventional headbands must wrap around the head, posing risks of pressure or displacement regardless of sleeping posture. By contrast, the system of the present disclosure enables convenient changes in body position, such as side sleeping or supine sleeping. Moreover, the introduction of the neck strap structure eliminates the need to loop a headband over the top portion 34 of the head; instead, the mask can be initially positioned simply by hanging around the neck, thereby making the operation more intuitive and particularly advantageous for elderly or mobility-impaired users. For patients with long hair, this system further avoids disturbing hairstyles or leaving pressure marks. Overall, this configuration provides a more ergonomic direction for the development of mask-type devices.
7. The flaps 36 of the nasal sealing region, in combination with the redesigned sealing points, provide synergistic advantages in terms of airtightness, structural stability, wearing comfort, and adaptability of the oronasal mask stabilization system 1. The flaps 36, as locally extended flexible conforming structures, enable more precise coverage and sealing compensation on both sides of the nasal alae, thereby effectively enhancing airtightness and preventing leakage caused by variations in facial morphology or dynamic facial expressions. At the same time, by relocating the top portion 34 of the sealing structure downward, the overall contact region avoids the nasal root and the areas of pronounced nasal dorsum height difference. This allows the flaps 36 to conform more closely to the natural curvature of the lateral nasal regions, further improving structural stability and comfort during wearing. The flaps 36 thereby provides a compensatory mechanism that greatly enhances the universality of the product across different patient populations and usage scenarios.

The technical features described in the foregoing embodiments may be combined in any manner. For the sake of brevity, all possible combinations of the technical features in the above embodiments are not described exhaustively. However, as long as such combinations do not present contradictions, they shall be considered within the scope of the present disclosure as set forth herein.

The embodiments described above merely illustrate several implementations of the present disclosure. Although the description is relatively specific and detailed, it should not be construed as limiting the scope of the invention. It should be understood that, for those skilled in the art, various modifications and improvements may be made without departing from the spirit and concept of the present disclosure, and all such modifications and improvements fall within the scope of protection of the present invention. Accordingly, the scope of protection of the present patent shall be defined by the appended claims.

It must be noted that as used herein and in the appended claims, the singular forms “a”, “an”, and “the” include their plural equivalents, unless the context clearly dictates otherwise.

The invention claimed is:

1. An oronasal mask stabilization system, configured to form a seal around a facial region of an airway inlet of a patient and to stabilize a breathable gas passage against the patient’s face, the oronasal mask stabilization system comprising:

a support member configured to have a curvature at least partially facing the patient;

a sealing formation structure configured to connect with the support member and seal against the patient’s face;

wherein the sealing formation structure is configured to have a top portion and a bottom portion, the top portion configured to contact a nasal bridge of the patient during use and to form a seal below a nasal root and above a nasal tip, and the bottom portion configured to contact and seal against a mandibular region of the patient, wherein the top portion is configured to form the seal at a position below 15% of an overall nasal bridge length measured from a radix and above 15% of the overall nasal bridge length measured from the nasal tip;

wherein the sealing formation structure has a first side in contact with the patient’s face and a second side connected to the support member, wherein the first side comprises at least one opening, the at least one opening comprises a nasal receiving region and an oral receiving region; and wherein the nasal receiving region at least comprises a nasal tip and nasal alae, and the nasal receiving region has flaps provided on the left and right sides, and the flaps are configured to conform to the nasal alae of the patient during use.

2. The oronasal mask stabilization system according to claim 1, wherein the support member comprises a main body portion and a mask stabilizer, and the mask stabilizer is configured to be connected to the main body portion in a front-to-back manner.

3. The oronasal mask stabilization system according to claim 2, wherein, in a front orthogonal view, a maximum distance between an outer contour of the mask stabilizer and an outer contour of the sealing formation structure is less than or equal to 3 mm.

4. The oronasal mask stabilization system according to claim 1, wherein the support member is at least partially a rigid member.

5. The oronasal mask stabilization system according to claim 1, wherein the sealing formation structure comprises at least three regions having different thicknesses.

6. An oronasal mask stabilization system, configured to form a seal around a facial region of an airway inlet of a patient and to stabilize a breathable gas passage against the patient’s face, the oronasal mask stabilization system comprising:

a support member configured to have a curvature at least partially facing the patient;

a sealing formation structure configured to connect with the support member and seal against the patient’s face;

wherein the sealing formation structure is configured to have a top portion and a bottom portion, the top portion configured to contact a nasal bridge of the patient during use and to form a seal below a nasal root and above a nasal tip, and the bottom portion configured to contact and seal against a mandibular region of the patient, wherein the top portion is configured to form the seal at a position below 15% of an overall nasal bridge length measured from a radix and above 15% of the overall nasal bridge length measured from the nasal tip;

wherein the sealing formation structure has a first side in contact with the patient’s face and a second side connected to the support member, wherein the first side comprises at least one opening, the at least one opening comprises a nasal receiving region and an oral receiving region;

wherein the nasal receiving region has a curvature at least in a portion provided at the edge of the opening, and the curvature extends toward the pressurized space; and wherein the sealing formation structure comprises at least three regions having different thicknesses, comprising thin regions at the top portion and the bottom portion, a thick region at an intermediate region between the first side and the second side, and a thickest region provided between the thick region and the second side.

7. The oronasal mask stabilization system according to claim 6, wherein the support member comprises a main body portion and a mask stabilizer, and the mask stabilizer is configured to be connected to the main body portion in a front-to-back manner.

8. The oronasal mask stabilization system according to claim 7, wherein, in a front orthogonal view, a maximum distance between an outer contour of the mask stabilizer and an outer contour of the sealing formation structure is less than or equal to 3 mm.

9. The oronasal mask stabilization system according to claim 6, wherein the thin region has a uniform wall thickness.

10. The oronasal mask stabilization system according to claim 6, wherein the thick region has a uniform wall thickness.

11. The oronasal mask stabilization system according to claim 6, wherein the sealing formation structure has a gradient wall thickness at least in part.

12. The oronasal mask stabilization system according to claim 6, wherein the sealing formation structure comprises four regions having different thicknesses.

13. An oronasal mask stabilization system, configured to form a seal around a facial region of an airway inlet of a patient and to stabilize a breathable gas passage against the patient’s face, the oronasal mask stabilization system comprising:

a support member configured to have a curvature at least partially facing the patient;

wherein the support member comprises a main body portion and a mask stabilizer, and the mask stabilizer is configured to be connected to the main body portion in a front-to-back manner;

a sealing formation structure, configured to connect with the support member and seal against the patient’s face;

wherein the sealing formation structure is configured to have a top portion and a bottom portion, the top portion configured to contact a nasal bridge of the patient during use and to form a seal below a nasal root and above a nasal tip, and the bottom portion configured to contact and seal against a mandibular region of the patient, wherein the top portion is configured to form the seal at a position below 15% of an overall nasal bridge length measured from a radix and above 15% of the overall nasal bridge length measured from the nasal tip;

wherein the sealing formation structure has a first side in contact with the patient's face and a second side connected to the support member, wherein the first side comprises at least one opening, the at least one opening comprises a nasal receiving region and an oral receiving region; and wherein the oronasal mask stabilization system has a width-to-length ratio of not greater than 1.5.

14. The oronasal mask stabilization system according to claim 13, wherein the main body portion is at least partially a flexible member.

15. The oronasal mask stabilization system according to claim 13, wherein the main body portion is at least partially a rigid member or a semi-rigid member.

16. The oronasal mask stabilization system according to claim 13, wherein the mask stabilizer is detachably connected to the main body portion.

17. The oronasal mask stabilization system according to claim 13, wherein the mask stabilizer is non-detachably connected to the main body portion.

18. The oronasal mask stabilization system according to claim 13, wherein the mask stabilizer is connected to the main body portion by mutually engaging configurations.

19. An oronasal mask stabilization system, configured to form a seal around a facial region of an airway inlet of a patient and to stabilize a breathable gas passage against the patient's face, the oronasal mask stabilization system comprising:

a support member configured to have a curvature at least partially facing the patient;

a sealing formation structure configured to connect with the support member and seal against the patient's face;

wherein the sealing formation structure is configured to have a top portion and a bottom portion, the top portion configured to contact a nasal bridge of the patient during use and to form a seal below a nasal root and above a nasal tip, and the bottom portion configured to contact and seal against a mandibular region of the patient, wherein the top portion is configured to form the seal at a position below 15% of an overall nasal bridge length measured from a radix and above 15% of the overall nasal bridge length measured from the nasal tip;

wherein the sealing formation structure has a first side in contact with the patient's face and a second side connected to the support member, wherein the first side has only one opening, and the at least one opening comprises a nasal receiving region and an oral receiving region; and wherein a length of the oronasal mask stabilization system ranges from 3 cm to 10.5 cm.

20. The oronasal mask stabilization system according to claim 19, wherein the support member comprises a main body portion and a mask stabilizer, and the mask stabilizer is configured to be connected to the main body portion in a front-to-back manner.

21. The oronasal mask stabilization system according to claim 20, wherein, in a front orthogonal view, a maximum distance between an outer contour of the mask stabilizer and an outer contour of the sealing formation structure is less than or equal to 3 mm.

22. The oronasal mask stabilization system according to claim 19, wherein the sealing formation structure comprises at least three regions having different thicknesses.

23. The oronasal mask stabilization system according to claim 19, wherein at least a portion of the sealing formation structure has an abrupt change in wall thickness.

* * * * *